United States Patent
Schneider et al.

(10) Patent No.: US 10,811,131 B2
(45) Date of Patent: Oct. 20, 2020

(54) SYSTEMS AND METHODS FOR INTELLIGENT PATIENT INTERFACE DEVICE

(71) Applicants: BAXTER INTERNATIONAL INC., Deerfield, IL (US); BAXTER HEALTHCARE S.A., Glattpark (Opfikon) (CH)

(72) Inventors: Dennis I. Schneider, Nashua, NH (US); Dennis A. Tribble, Ormond Beach, FL (US); Matthew A. Valentine, Ormond Beach, FL (US)

(73) Assignees: BAXTER INTERNATIONAL INC., Deerfield, IL (US); BAXTER HEALTHCARE SA, Glattpark (Opfikon) (CH)

( * ) Notice: Subject to any disclaimer, the term of this patent is extended or adjusted under 35 U.S.C. 154(b) by 423 days.

(21) Appl. No.: 15/900,322

(22) Filed: Feb. 20, 2018

(65) Prior Publication Data
US 2018/0174676 A1     Jun. 21, 2018

Related U.S. Application Data

(63) Continuation of application No. 13/485,634, filed on May 31, 2012, now Pat. No. 9,934,540.
(Continued)

(51) Int. Cl.
*G16H 20/17* (2018.01)
*G06Q 10/10* (2012.01)
(Continued)

(52) U.S. Cl.
CPC ........... *G16H 20/17* (2018.01); *G06F 19/326* (2013.01); *G06Q 10/10* (2013.01); *G06Q 50/24* (2013.01);
(Continued)

(58) Field of Classification Search
CPC .............................. G16H 20/17; G06Q 50/24
(Continued)

(56) References Cited

U.S. PATENT DOCUMENTS

| 4,847,764 A | 7/1989 | Halvorson |
| 5,078,683 A | 1/1992 | Sancoff et al. |

(Continued)

FOREIGN PATENT DOCUMENTS

| WO | 2005031631 A2 | 4/2005 |
| WO | 2005050526 A2 | 6/2005 |
| WO | 2002069099 A1 | 9/2005 |

OTHER PUBLICATIONS

Google.com search, Jun. 11, 2020 (Year: 2020).*
ip.com search, Jun. 11, 2020 (Year: 2020).*

*Primary Examiner* — Dilek B Cobanoglu
(74) *Attorney, Agent, or Firm* — K&L Gates LLP

(57) ABSTRACT

A system for use with one or more sources of patient-affiliated data corresponding with a group of patients. The system may contain a plurality of patient interface devices for interfacing with the group of patients. Each patient interface device may store a database that includes information related to each patient of the group of patients. Each patient interface device may be operable to generate a patient-specific guidance data set that may be used by the patient interface device to interface with a patient of the group of patients. The plurality of patient interface devices may be communicatively coupled to patient-affiliated data and a therapy database via a patient interface device gateway. The patient-specific guidance data sets may be automatically updated.

20 Claims, 5 Drawing Sheets

Related U.S. Application Data

(60) Provisional application No. 61/503,966, filed on Jul. 1, 2011.

(51) Int. Cl.
  *G06F 19/00* (2018.01)
  *G06Q 50/24* (2012.01)
  *G16H 10/60* (2018.01)
  *G16H 70/00* (2018.01)
  *G16H 10/40* (2018.01)
  *G16H 50/20* (2018.01)

(52) U.S. Cl.
  CPC ............ *G16H 10/40* (2018.01); *G16H 10/60* (2018.01); *G16H 70/00* (2018.01); *G06F 19/3468* (2013.01); *G16H 50/20* (2018.01)

(58) Field of Classification Search
  USPC .......................................................... 705/3
  See application file for complete search history.

(56) References Cited

U.S. PATENT DOCUMENTS

| | | | |
|---|---|---|---|
| 5,100,380 A | | 3/1992 | Epstein et al. |
| 5,181,910 A | * | 1/1993 | Scanlon ................ A61M 5/172 |
| | | | 128/DIG. 12 |
| 5,368,562 A | | 11/1994 | Blomquist et al. |
| 5,558,638 A | | 9/1996 | Evers et al. |
| 5,573,506 A | | 11/1996 | Vasko |
| 5,609,575 A | | 3/1997 | Larson et al. |
| 5,619,569 A | | 4/1997 | McVay et al. |
| 5,630,710 A | | 5/1997 | Tune et al. |
| 5,643,212 A | | 7/1997 | Coutre et al. |
| 5,658,250 A | | 8/1997 | Blomquist et al. |
| 5,681,285 A | | 10/1997 | Ford et al. |
| 5,713,856 A | * | 2/1998 | Eggers ................ A61M 5/1413 |
| | | | 604/65 |
| 5,772,635 A | * | 6/1998 | Dastur ................. A61M 5/172 |
| | | | 604/131 |
| 5,781,442 A | * | 7/1998 | Engleson ............... G16H 40/20 |
| | | | 700/214 |
| 5,795,327 A | * | 8/1998 | Wilson ................. A61M 5/172 |
| | | | 604/65 |
| 5,807,336 A | | 9/1998 | Russo et al. |
| 5,814,015 A | | 9/1998 | Gargano et al. |
| 5,836,910 A | | 11/1998 | Duffy et al. |
| 5,845,255 A | | 12/1998 | Mayaud |
| 5,871,465 A | | 2/1999 | Vasko |
| 5,885,245 A | | 3/1999 | Lynch et al. |
| 5,895,371 A | * | 4/1999 | Levitas ................ A61M 5/1723 |
| | | | 604/500 |
| 5,941,846 A | | 4/1999 | Duffy et al. |
| 5,940,802 A | | 8/1999 | Hildebrand et al. |
| 5,946,659 A | | 8/1999 | Lancelot et al. |
| 6,053,887 A | | 4/2000 | Levitas et al. |
| 6,135,949 A | | 10/2000 | Russo et al. |
| 6,228,057 B1 | | 5/2001 | Vasko |
| 6,241,704 B1 | | 6/2001 | Peterson et al. |
| 6,317,719 B1 | | 11/2001 | Schrier et al. |
| 6,468,242 B1 | * | 10/2002 | Wilson ................. A61M 5/172 |
| | | | 604/65 |
| 6,551,243 B2 | | 4/2003 | Bocionek et al. |
| 6,671,563 B1 | | 12/2003 | Engelson et al. |
| 6,689,091 B2 | | 2/2004 | Bui et al. |
| 6,790,198 B1 | | 9/2004 | White et al. |
| 6,915,170 B2 | | 7/2005 | Bocionek et al. |
| 6,999,854 B2 | | 2/2006 | Roth |
| 7,025,743 B2 | | 4/2006 | Mann et al. |
| 7,074,205 B1 | | 7/2006 | Duffy et al. |
| 7,076,435 B1 | | 7/2006 | McKeag et al. |
| 7,171,277 B2 | | 1/2007 | Engleson et al. |
| 7,171,992 B2 | | 2/2007 | DiGianfilippo et al. |
| 7,194,336 B2 | | 3/2007 | DiGianfilippo et al. |
| 7,204,823 B2 | | 4/2007 | Estes et al. |
| 7,317,967 B2 | | 1/2008 | DiGianfilippo et al. |
| 7,343,224 B2 | | 3/2008 | DiGianfilippo et al. |
| 7,349,858 B1 | | 3/2008 | McGrady et al. |
| 7,426,476 B2 | | 9/2008 | Munoz et al. |
| 7,464,042 B2 | | 12/2008 | Beraja et al. |
| 7,471,994 B2 | | 12/2008 | Ford et al. |
| 7,493,264 B1 | | 2/2009 | Kelly et al. |
| 7,509,264 B2 | | 3/2009 | Hasan et al. |
| 7,520,419 B2 | | 4/2009 | Libin et al. |
| 7,535,336 B2 | | 5/2009 | Willems et al. |
| 7,536,309 B1 | | 5/2009 | Vasko et al. |
| 7,578,432 B2 | | 8/2009 | Libin et al. |
| 7,630,908 B1 | | 12/2009 | Amrien et al. |
| 7,654,976 B2 | | 2/2010 | Peterson et al. |
| 7,672,973 B2 | | 3/2010 | Lordo |
| 7,698,156 B2 | | 4/2010 | Martucci et al. |
| 7,707,047 B2 | | 4/2010 | Hasan et al. |
| 7,711,583 B2 | | 5/2010 | Epstein et al. |
| 7,771,385 B2 | | 8/2010 | Eggers et al. |
| 7,778,852 B2 | | 8/2010 | Vasko et al. |
| 7,792,689 B2 | | 9/2010 | Duckert |
| 7,813,714 B2 | | 10/2010 | Laursen et al. |
| 7,815,602 B2 | | 10/2010 | Mann et al. |
| 7,835,927 B2 | * | 11/2010 | Schlotterbeck ....... G06F 19/325 |
| | | | 705/3 |
| 7,860,583 B2 | | 12/2010 | Condurso et al. |
| 7,870,249 B2 | | 1/2011 | Brown |
| 7,895,053 B2 | | 2/2011 | Holland et al. |
| 7,933,780 B2 | | 4/2011 | De La Huerga |
| 8,005,688 B2 | * | 8/2011 | Coffman ............ G06F 19/3462 |
| | | | 705/2 |
| 8,020,564 B2 | * | 9/2011 | Batch .................... A61B 5/411 |
| | | | 128/897 |
| 8,357,114 B2 | * | 1/2013 | Poutiatine ............. A61J 7/0038 |
| | | | 604/59 |
| 8,359,338 B2 | * | 1/2013 | Butterfield .......... G06F 19/3456 |
| | | | 707/803 |
| 8,499,966 B2 | * | 8/2013 | Palmer ................ G07F 17/0092 |
| | | | 221/232 |
| 9,135,393 B1 | * | 9/2015 | Blomquist ............. G06F 21/00 |
| 2002/0116509 A1 | * | 8/2002 | DeLaHuerga ........ G06F 19/326 |
| | | | 709/229 |
| 2004/0172300 A1 | | 9/2004 | Mihai et al. |
| 2005/0065817 A1 | | 3/2005 | Mihai et al. |
| 2005/0107913 A1 | | 5/2005 | Engleson et al. |
| 2005/0113945 A1 | | 5/2005 | Engleson et al. |
| 2005/0246416 A1 | * | 11/2005 | Blomquist .......... G06F 19/3468 |
| | | | 709/203 |
| 2006/0026205 A1 | | 2/2006 | Butterfield |
| 2006/0100746 A1 | | 5/2006 | Leibner-Druska |
| 2006/0116639 A1 | * | 6/2006 | Russell ............... G06F 19/3418 |
| | | | 604/131 |
| 2006/0265246 A1 | | 11/2006 | Haag |
| 2007/0016476 A1 | | 1/2007 | Hoffberg et al. |
| 2007/0053513 A1 | | 3/2007 | Hoffberg |
| 2007/0124177 A1 | | 5/2007 | Engleson et al. |
| 2007/0168461 A1 | | 7/2007 | Moore |
| 2007/0255250 A1 | | 11/2007 | Moberg et al. |
| 2008/0033361 A1 | | 2/2008 | Evans et al. |
| 2008/0033402 A1 | | 2/2008 | Blomquist |
| 2008/0071209 A1 | | 3/2008 | Moubayed et al. |
| 2008/0125897 A1 | | 5/2008 | DiGianfilippo et al. |
| 2008/0154177 A1 | * | 6/2008 | Moubayed .......... G06F 19/3468 |
| | | | 604/19 |
| 2008/0249386 A1 | | 10/2008 | Besterman et al. |
| 2008/0269673 A1 | | 10/2008 | Butol et al. |
| 2009/0076461 A1 | | 3/2009 | Susi et al. |
| 2009/0125336 A1 | | 5/2009 | Wehba et al. |
| 2010/0030387 A1 | | 2/2010 | Sen |
| 2010/0121654 A1 | * | 5/2010 | Portnoy ................. G16H 20/17 |
| | | | 705/3 |
| 2010/0160860 A1 | | 6/2010 | Celentano et al. |
| 2010/0168660 A1 | | 7/2010 | Galley et al. |
| 2010/0191543 A1 | | 7/2010 | Shuman |
| 2010/0222845 A1 | | 9/2010 | Goetz |
| 2010/0240964 A1 | | 9/2010 | Sterling et al. |
| 2010/0268157 A1 | | 10/2010 | Wehba et al. |

(56) References Cited

U.S. PATENT DOCUMENTS

| | | |
|---|---|---|
| 2010/0273738 A1* | 10/2010 | Valcke .................. A61B 5/155 |
| | | 514/56 |
| 2010/0280486 A1 | 11/2010 | Khair et al. |
| 2010/0292556 A1 | 11/2010 | Golden |
| 2010/0299517 A1 | 11/2010 | Jukic et al. |
| 2010/0318699 A1 | 12/2010 | Gao-Saari et al. |
| 2010/0332257 A1 | 12/2010 | Sims et al. |
| 2011/0011167 A1 | 1/2011 | Gable et al. |
| 2011/0028901 A1 | 2/2011 | Estes et al. |
| 2011/0040247 A1 | 2/2011 | Mandro et al. |
| 2011/0071844 A1* | 3/2011 | Cannon ............... G06F 19/3468 |
| | | 705/2 |

* cited by examiner

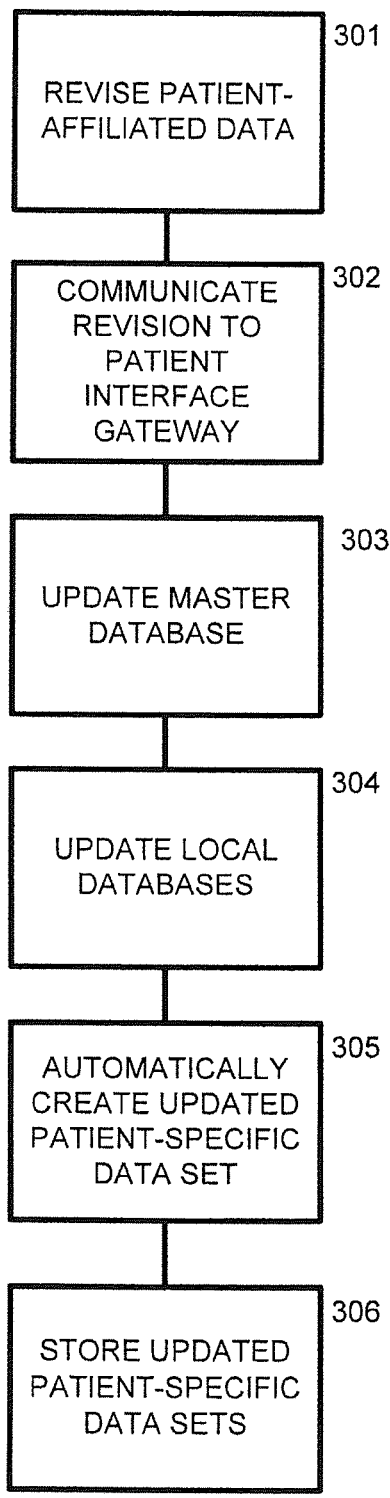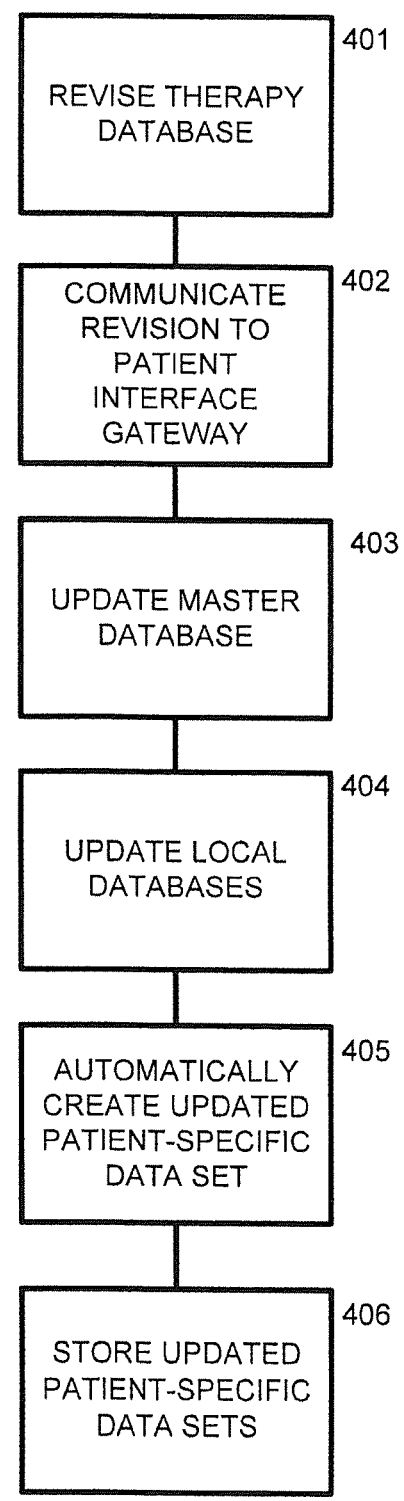
FIG. 3
FIG. 4

SYSTEMS AND METHODS FOR INTELLIGENT PATIENT INTERFACE DEVICE

PRIORITY CLAIM

This application is a continuation of U.S. patent application Ser. No. 13/485,634 filed May 31, 2012, entitled "SYSTEMS AND METHODS FOR INTELLIGENT PATIENT INTERFACE DEVICE," which claims priority to U.S. Provisional Patent Application No. 61/503,966 filed Jul. 1, 2011, entitled "SYSTEMS AND METHODS FOR INTELLIGENT PATIENT INTERFACE DEVICE," the entire contents of each of which are incorporated herein by reference.

FIELD OF THE INVENTION

The present invention relates to systems and methods for the provision of medical services to a group of patients, and more particularly, to systems and methods for control of intelligent patient interface devices adapted to interface with one or more patients of the group of patients.

BACKGROUND OF THE INVENTION

Patient interface devices used in the field of health care may be used to administer medication and/or therapy and/or monitor an attribute of a patient. In particular, infusion pumps as used in the field of health care are electromechanical devices which control the flow rate of liquid medications and foodstuffs. Infusion pumps may include a mechanical actuator capable of displacing a syringe plunger to expel fluid from a syringe. Other types of infusion pumps may use other mechanisms to effectuate the delivery of fluids.

In veterinary and human health care, infusion pumps are used in the delivery of chemicals, drugs, nutrition, or other products to patients. Typically, one or more substances are combined to form a solution containing one or more medications and are then delivered by an infusion pump to a patient. Such delivery may be into the bloodstream of the patient from a medication source via tubing and an interconnected catheter or into the gut or directly into tissue.

Typically, infusion pumps are capable of controlling the flow rate of the medication to the patient according to a predetermined programmable pattern. Such delivery may be continuous or intermittent. A particular pattern of delivery may be dependent on a combination of local practices, the type of medication being delivered and attributes of the patient.

The process of determining a proper protocol for medication delivery to a patient is often complex and errors may reduce efficacy and may be potentially harmful to patients. As such, automated logic devices have been developed to facilitate the determination and application of medication delivery protocols. Such logic devices have been implemented in infusion pumps to realize improved medication delivery. When implemented in this manner, the infusion devices have been referred to as "smart pumps." To date, however, systems have not been deployed which recognize, generate and apply the full extent of data employable to further enhance automated facets of medication delivery. Specifically, these systems are either contextually unaware of patient details when computing safety limits on medication infusions, or limit their contextual awareness to a query of patient databases (such as an electronic medical record, also called an EMR, EHR, or eMAR) while initiating the infusion of medication therapy. In order to maintain this limited contextual awareness, these systems must be continuously connected to the patient databases by wired or wireless means in order to function properly. As such they are not tolerant of losses of connectivity due to network failure or poor wireless communication coverage.

SUMMARY OF THE INVENTION

In view of the foregoing, an objective of the present invention is to provide apparatus and methods for the provision of medical services to one or more patients of a group of patients.

Another objective is to provide apparatus and methods for the provision of medical services using one or more of a plurality of communicatively interconnected patient interface devices.

Another objective is to provide apparatus and methods for the management of patient databases for a group of patients where the entirety of the patient databases are stored on each patient interface device of a plurality of communicatively interconnected patient interface devices.

One or more of the above-noted objectives and additional advantages may be realized by an inventive system for use with one or more sources of patient-affiliated data corresponding with a group of patients that includes a plurality of patient interface devices, each for interfacing with a patient for the provision of medical care. Each patient interface device of the plurality of patient interface devices stores a database that comprises a plurality of patient records where each patient record of the plurality of patient records is related to a unique patient of the group of patients. In this regard, any patient interface device of the plurality of patient interface devices may be used with any patient of the group of patients, thus reducing or eliminating the need to have a specific patient interface device assigned to and/or follow a specific patient.

The system further includes a patient interface device gateway operative to interface the one or more sources of patient-affiliated data with each patient interface device of the plurality of patient interface devices to automatically update the databases stored at each patient interface device. Such automatic updating of the databases is achieved by utilizing corresponding patient-affiliated data maintained by the one or more sources of patient-affiliated data. In this regard, the databases in each patient interface device may be maintained such that each patient interface device comprises data that may be used by the patient interface device to create patient-specific guidance data sets which may be used by the patient interface device to control the patient interface device while it is interfacing with a patient.

In various embodiments: at least a portion of the plurality of patient interface devices may each be operable to administer medical treatment to a patient; at least a portion of the plurality of patient interface devices may each be operable to administer medication to a patient; at least a portion of the plurality of patient interface devices may each be operable to administer liquid medication to a patient; and at least a portion of the plurality of patient interface devices each may comprise an infusion pump.

In one approach, all of the plurality of patient interface devices each may comprise an infusion pump. In another approach, at least a portion of the plurality of patient interface devices may each be operable to monitor at least one attribute of a patient.

In one approach, the group of patients may comprise patients admitted in a medical care facility, such as for example, a clinic or hospital. In this regard, the group of patients may be patients in a medical care facility who have been prescribed care using a patient interface device, for example, who have been prescribed a medication for infusion pump administration.

The patient-affiliated data may include one or more databases. Such databases may be administered by the facility in which the system is located and may include one or more of the following types of databases: an Electronic Medical Records (EMR) database, a pharmacy database; a hospital medical record database; a medication administration record database; and an admission, discharge and transfer database. Other appropriate databases may also be included.

In an embodiment, the system may further include logic adapted to create a patient-specific guidance data set for any patient of the group of patients. Such a patient-specific guidance data set may be adapted for use in interfacing the patient interface device with the corresponding patient. The logic may be capable of automatically updating a patient-specific guidance data set in response to a change in the patient-affiliated data. In an approach, the system may further include a therapy database and the logic may be capable of automatically updating the patient-specific guidance data set in response to a change in the therapy database. The logic may determine the updated patient-specific guidance data set based on therapy data (including medication data) stored in the therapy database and the patient-affiliated data. Each patient interface device of the plurality of patient interface devices may include such logic.

Further, each of the patient interface devices may include an input. Changes in the patient-affiliated data may originate from the input of one of the plurality of patient interface devices. In this regard, the input may be of any appropriate form, including for example, a barcode reader, a card reader (e.g., capable of reading a magnetic strip on a card), an RFID reader, a keyboard, a key pad, a touch screen (e.g., with a menu-driven interface), a data port and/or a wireless adapter. Changes in the patient-affiliated data may originate from a source other than one of the plurality of patient interface devices, such as for example, a terminal interconnected to the pharmacy database or any other database.

In a variation, each of the plurality of patient interface devices may be adapted to send data related to its performed actions to the one or more sources of patient-affiliated data via the patient interface device gateway. In this regard, patient-affiliated data may reflect actions performed by the plurality of patient interface devices. For example, where at least a portion of the plurality of patient interface devices are infusion pumps, each such infusion pump may be adapted to transfer pump-specific data sets to a pump surveillance database that may be part of the system. The pump-specific data sets may include data related to pump performance, such as run time and/or volume of medication pumped. The pump surveillance database may be used to track infusion pump performance and determine maintenance and/or replacement intervals.

By way of example, the patient interface device gateway may include a communication link to the one or more sources of patient-affiliated data, a communication link to the therapy database, and communication links to each patient interface device of the plurality of patient interface devices. The patient interface device gateway may also include a communication link to an external global therapy database. In an implementation, the patient interface device gateway may be in the form of a server.

In another aspect, a method of updating a patient-specific guidance data set related to a patient is disclosed. The patient-specific guidance data set is disposed within a first patient interface device, and is adapted for use in interfacing the first patient interface device with a corresponding patient. The method includes entering information related to a patient into the first patient interface device, then automatically transferring, over a patient interface device gateway, the information from the first patient interface device to one or more sources of patient-affiliated data. The method further includes revising the one or more sources of patient-affiliated data with the information to create updated patient-affiliated data and automatically updating the patient-specific guidance data set related to the patient to create an updated patient-specific guidance data set related to the patient. The updating is performed by logic disposed within the first patient interface device and is based on data within a therapy database and the updated patient-affiliated data. The method further includes storing on the first patient interface device the updated patient-specific guidance data set related to the patient and storing data related to the updated patient-affiliated data on each patient interface device of a plurality of other patient interface devices communicatively interconnected to the patient interface device gateway.

In an embodiment, the method may further include entering patient identification information of the patient into the first patient interface device, then accessing the updated patient-specific guidance data set related to the patient in response to the entering patient identification information step, and administering medical care to the patient according to the updated patient-specific guidance data set related to the patient. In a variation, the administering medical care may comprise: administering medical treatment to a patient; administering medication to a patient; and/or administering liquid medication to a patient. In a variation, the administering medical treatment may include infusing liquid medication into the patient where the patient interface device is an infusion pump.

In an embodiment, each patient interface device of the plurality of other patient interface devices may include logic adapted to generate the updated patient-specific guidance data set related to the patient and the method may further include one of these other patient interface devices generating, by the included logic, the updated patient-specific guidance data set related to the patient. Such generating may be based on data within a therapy database and the updated patient-affiliated data.

In still another aspect, a method of updating a plurality of patient interface device databases is provided. Each patient interface device database of the plurality of patient interface device databases comprises data related to a plurality of patients and is disposed within a unique patient interface device of a plurality of patient interface devices. Each patient interface device of the plurality of patient interface devices is communicatively interconnected to a patient interface device gateway. The method includes revising patient-affiliated data with information related to a patient of the plurality of patients to create updated patient-affiliated data, then updating a master database to create an updated master database, and then updating each patient interface device database.

In yet another aspect, a method of updating a plurality of patient interface device databases is provided. Each patient interface device database includes data related to a plurality of patients. Each patient interface device database is disposed within a unique patient interface device of a plurality of patient interface devices. The method of the current aspect includes revising a therapy database with information related to a medication to create a revised therapy database, then updating a master database to create an updated master database, and, based on the updated master database, updating each patient interface device database.

Another aspect provides for a patient interface device that comprises an input, a computer readable memory adapted to store a database, logic adapted to select a record within the database based on patient identification information received at the input, logic adapted to generate a patient-specific guidance data set associated with a patient based on the record, and logic adapted to control the patient interface device according to information stored in the patient-specific guidance data set associated with the patient. The input is adapted to receive patient identification information.

In an approach, the patient interface device may include a data interface that is operable to send and receive data related to changes in patient-affiliated data to a computer network. The patient interface device may include logic that is adapted to generate a patient-specific guidance data set from information obtained from a therapy database and the patient-affiliated data via the data interface. The data interface may be a wireless interface. The input may be operable to receive information in the form of a bar code, an RFID tag, a name, a serial number, an identification number, a signal from an embedded identification device, and/or an identification card.

In still another aspect, a plurality of patient interface devices are provided that include first and second patient interface devices. The first patient interface device includes a first computer readable memory, a database, and logic. The database is stored in the first computer readable memory and includes a first record associated with a first patient and a second record associated with a second patient.

The logic is operable to create a first patient-specific guidance data set based on the first record and associated with the first patient. The first patient-specific guidance data set is adapted for use in interfacing any of the plurality of patient interface devices with the first patient. The logic is also operable to create a second patient-specific guidance data set based on the second record and associated with the second patient. The second patient-specific guidance data set is adapted for use in interfacing any of the plurality of interface devices with the second patient. The plurality of patient interface devices further includes a second patient interface device that includes a second computer readable memory, a copy of the database stored in the second computer readable memory, and a copy of the logic.

Such a plurality of patient interface devices allows for any one of a number of patient devices to be used with a particular patient, since each patient interface device may be capable of employing its logic to the database stored on the patient interface device to create a patient-specific guidance data set. For example, where the plurality of patient interface devices includes a plurality of infusion pumps, any one of the plurality of infusion pumps may be employed to infuse a medication into a patient. Such employment may be performed without the need for the selected infusion pump to have any additional data loaded into it prior to use infusing medication into the patient. This is possible since the database includes all the necessary data related to the patient and the logic includes the necessary intelligence to determine an appropriate infusion profile based on such data.

In another aspect, a system is provided for use with one or more sources of patient-affiliated data corresponding with a group of patients. The system includes logic and a patient interface device gateway. The logic is adapted to create a plurality of patient-specific guidance data sets based on therapy data stored in a therapy database and patient data stored in the one or more sources of patient-affiliated data. Each patient-specific guidance data set is associated with a unique patient. The patient interface device gateway is adapted to interface the logic with the one or more sources of patient-affiliated data and the therapy database. The patient interface device gateway is further adapted to send copies of data within the one or more sources of patient-affiliated data and/or the therapy database to each patient interface device of a plurality of patient interface devices.

An additional aspect is provided that is a method of operating a patient interface device. The method includes entering identification information for a first patient into the patient interface device and then automatically generating a first patient-specific guidance data set from a database resident within the patient interface device. The first patient-specific guidance data set is adapted for use in interfacing the patient interface device to the first patient. The method further includes interfacing the patient interface device with the first patient according to parameters within the first patient-specific guidance data set. Such interfacing, for example, may include monitoring an attribute of the patient and/or administering a medication to the patient.

In an embodiment of the present aspect, the method may further include entering identification information for a second patient into the patient interface device, then automatically generating a second patient-specific guidance data set from the database resident within the patient interface device, and then interfacing the patient interface device with the second patient according to parameters within the second patient-specific guidance data set. The method, including interfacing with both the first and second patients, may be performed without any communication between the patient interface device and an external database or external device.

In another aspect, a method of managing data in a system that comprises a plurality of patient interface devices is provided. The method includes receiving data at a patient interface device gateway and updating a master database based on the data received. The updating includes a first set of changes to the master database. The method further includes broadcasting the first set of changes to the plurality of patient interface devices and, for each patient interface device, updating a database resident in the patient interface device with the first set of changes.

In an embodiment, the method further includes sending a first subset of the received data to a first database and sending a second subset of the received data to a second database. The first and second databases are each unique databases that comprise patient-affiliated data. For example, the first database may be a pharmacy database and the second database may be an EMR database.

In another embodiment, the method may further include sending a first subset of the received data to a first database and sending a second subset of the received data to a second database, where the first subset of data is related to patient status, and the second subset of data is related to patient interface device status. For example, where the patient interface device is an infusion pump, the first subset of data may include information regarding the delivery of medication to the patient, such as delivery time and date, medication type, dosage, administration rate, and caregiver identification, while the second subset of data may include information regarding the performance of the patient interface device, such as number of strokes performed and infusion pump serial number.

In still another aspect, a method of operating a patient interface device is provided that includes identifying the presence of a predetermined condition indicative of a lack of currency of data stored within the patient interface device. The identifying is performed by the patient interface device. In this regard, the patient interface device may be operable to identify a number of unique predetermined conditions, any one of which could indicate a lack of currency of data stored within the patient interface device.

In an embodiment, the method may further include alerting a user to the lack of currency of data stored within the patient interface device. The alerting may be performed by the patient interface device and may, for example, be in the form of a visual or audible signal. Such alerting may be in response to the identification of the lack of currency of the data. In a variation, the patient interface device may prevent the user from using the patient interface device to interface with a patient. In another variation, the patient interface device may delete at least a portion of the data stored within the patient interface device.

In an embodiment, the identified predetermined condition may be the passage of a predetermined amount of time from the receipt, by the patient interface device, of a communication from a patient interface device gateway without the receipt of a subsequent communication from the patient interface device gateway. Once such a predetermined amount of time has passed without receiving a subsequent communication from the patient interface device gateway, the patient interface device may react by alerting a user, preventing a user from using the patient interface device to interface with a patient, and/or deleting at least a portion of the data stored within the patient interface device. In an example, the length of the predetermined amount of time may be assigned to the patient interface device based on the type of the patient interface device. In another example, a common predetermined length of time may be assigned to each patient interface device of a particular group, such as a medical facility. In a variation, the patient interface device may first react by preventing a user from using the patient interface device to interface with a patient, and, if no receipt of a subsequent communication from the patient interface device gateway occurs within a second predetermined amount of time, the patient interface device may then delete at least a portion of the data stored within the patient interface device. The second predetermined amount of time may be determined in a manner similar to that of the first predetermined amount of time.

In another embodiment, the identified predetermined condition may be based on the lack of reception of a serialized communication from a patient interface device gateway. In this regard, the method may include receiving, by the patient interface device prior to the identifying step, a first communication from a patient interface device gateway and a second communication from the patient interface device gateway. Both the first communication and the second communication may include serialized identifications. In such an embodiment, the identifying step may include determining, by the patient interface device and based on the first and second serialized identifications, the absence of one or more communications with serialized identifications between the first and second serialized identifications. Once such a predetermined condition (one or more missing communications) has been identified, the patient interface device may react by requesting the missing communications from the patient interface device gateway, alerting a user as to the missing communications, preventing a user from using the patient interface device to interface with a patient, and/or deleting at least a portion of the data stored within the patient interface device.

Numerous additional features and advantages of the present invention will become apparent to those skilled in the art upon consideration of the embodiment descriptions provided hereinbelow.

BRIEF DESCRIPTION OF THE DRAWINGS

FIG. 3 is a flowchart of a method of updating a patient-specific guidance data set by inputting data into patient-affiliated data.

FIG. 4 is a flowchart of a method of updating a patient-specific guidance data set by inputting data into a therapy database.

DETAILED DESCRIPTION

Figure 1A:
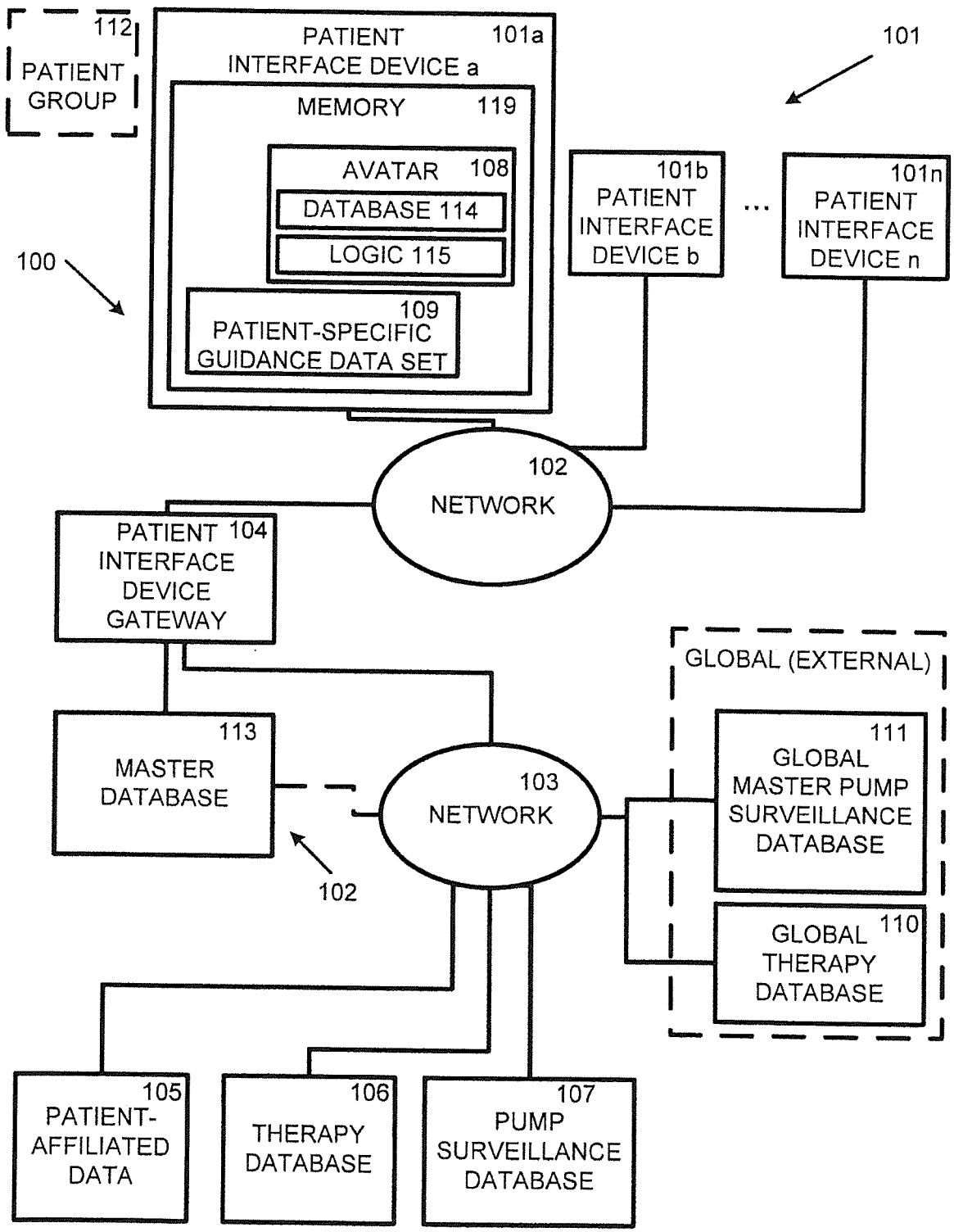
FIG. 1A illustrates a system for interfacing with patients and managing data that includes a plurality of patient interface devices.

FIG. 1A illustrates an intelligent system 100 for interfacing with a patient (e.g., administering medications such as medical fluids using an infusion pump or inhalants to a patient, administering therapy to a patient, or monitoring patient attributes) and managing data in a given medical care facility or network of medical care facilities. The data managed includes, for example, data related to types of medication, data related to the administration of medications, data related to therapy delivered, patient related data (e.g., identification data, patient attributes), and system performance data.

Generally the system 100 includes a plurality of patient interface devices 101 that includes patient interface devices 101a, 101b ... 101n, where n is any appropriate integer for a particular facility. More than one patient interface device may be associated with a particular patient. Each patient interface device of the plurality of patient interface devices 101 may be capable of interfacing with a patient in an automated fashion in that each may be programmed to deliver medication or therapy, or monitor the patient and once initiated, may perform at least a portion of the function without further input. For example, in the case where the patient interface device 101a is an infusion pump, the infusion pump may be operable to deliver a liquid medication to a patient by pumping the liquid medication through a catheter inserted into the patient.

Each patient interface device of the plurality of patient interface devices 101 may include a memory 119 in which patient-specific guidance data sets 109 may be stored. Each patient interface device may include input and output components to facilitate the transfer of information into and out of the patient interface devices 101. Each patient interface device may include at least one network connection enabling connection to a patient interface device network 102 or other patient interface devices 101 through, for example, a wired or wireless connection.

The patient interface device network 102 may facilitate a communicative interconnection of the plurality of patient interface devices 101 to a patient interface device gateway 104. The patient interface device gateway 104 may be in the form of a server. The patient interface device gateway 104 may be communicatively interconnected (e.g., through a network 103) to patient-affiliated data 105 that includes information related to specific individual patients. The patient interface device gateway 104 may also be communicatively interconnected to a therapy database 106 that includes information related to various therapies, including medications, such as formularies containing details about formulation of medications and administration practices for various types of medications. The patient interface device gateway 104 may also be communicatively interconnected to a pump surveillance database 107, which may include information related to the performance of a portion of the plurality of patient interface devices 101 that include infusion pumps. The patient interface device gateway 104 may also be communicatively interconnected to any other appropriate database such as other databases that a medical facility may maintain.

The system 100 may be comprised of a single type of patient interface device 101. For example, in an exemplary system, all of the patient interface devices 101 of the system 100 may be infusion pumps. In such a system, the patient interface device gateway 104 may be referred to as an infusion pump gateway.

A master database 113 may be communicatively interconnected to the patient interface device gateway 104. The master database 113 may include data used to operate the patient interface devices 101. For example, the master database 113 may include information from the patient-affiliated data 105 and/or the therapy database 106 that is pertinent to the operation of the patient interface devices 101. As an example, where one or more of the patient interface devices 101 are infusion pumps, the master database 113 may include information about a patient's condition and information about medications prescribed to the patient. The master database 113 may also include data regarding personnel working at the facility where it is being used. Such data may be used to identify or verify the identity of personnel operating the patient interface devices 101. The patient interface device gateway 104 may facilitate the maintenance of the currency of the master database 113 as described below.

The system 100 may include one or more avatars 108. Each avatar 108 may be located in the memory 119 of the patient interface devices. Each avatar 108 may comprise a database 114 and logic 115. The database 114 may include data from the master database 113. For example, the database 114 may be a copy of the master database 113 and the database 114 may be periodically updated to maintain parity with the master database 113. In this regard, any changes to the master database 113 may be communicated to the database 114 of each avatar 108.

The logic 115 of the avatar 108 may be capable of constructing patient-specific guidance data sets 109 from information disposed in the database 114. For example, where the patient-specific guidance data sets 109 are to include information about the administration of medication (e.g., where the patient interface device 101a is an infusion pump), the logic 115 of the avatar 108 may be capable of constructing patient-specific guidance data sets 109 in the form of infusion parameters from information disposed in the database 114 related to the patient and the particular medication to be administered.

The system 100 may be operable to interface with databases external to the system 100, such as a global therapy database 110 and a global master pump surveillance database 111, each of which is discussed below.

Turning to the patient-affiliated data 105, the patient-affiliated data 105 may contain data for a patient group 112. Such patient-affiliated data 105 may include information about individual patients of the patient group 112. The patient group 112 may, for example, be a group of patients currently admitted to a particular hospital or facility, or it may be a subset of such a group, such as patients currently admitted to a particular department of a hospital or patients admitted to a particular hospital who have been prescribed infusion treatments. In another example, the patient group 112 may be a group of patients currently admitted to a particular network of hospitals and/or other facilities that are under common management. The facilities may, for example, be hospitals, specialized treatment centers, clinics, outpatient facilities, physician's offices, mobile treatment facilities, individual homes of patients, or any other appropriate place or places where patients may receive infusions of medications. The patient group 112 may also include future or past patients, such as patients scheduled to be admitted to a particular facility or patients who had previously been admitted to a particular facility. The information about individual patients of the patient group 112 contained in the patient-affiliated data 105 may include, but not be limited to, identification data (e.g., name, address, identification numbers), medical history, medication history, and current health status.

The patient-affiliated data 105 may include multiple data sources located at multiple locations. The patient-affiliated data 105 may include any appropriate database that a hospital may access to determine how to treat a patient, including patient information pertinent to dosages of medications that may be administered to a patient. The patient-affiliated data 105 may include a facility's (e.g., a hospital's) medical record database or a portion thereof.

For example, the patient-affiliated data 105 may include a pharmacy database that contains data related to the medications currently prescribed for and previously administered to a particular patient along with any information regarding drug allergies, interactions between drugs, and appropriate dosing. The pharmacy database may include any other appropriate information.

For example, the patient-affiliated data 105 may include an Electronic Medical Records (EMR) database maintained by a facility. In another example, the patient-affiliated data 105 may include a database that includes Medication Administration Records (MARs) which may serve as the legal record of the drugs administered to the patients at a facility. In another example, the patient-affiliated data 105 may include a database that includes Admission, Discharge and Transfer (ADT) information.

The patient-affiliated data 105 may be disposed in a single computer system or it may be distributed among a plurality of computer systems. In this regard, each of the above-discussed components of the patient-affiliated data 105 may each be disposed on one or more separate computer systems. Thus, the pharmacy database may be disposed on a server located in a pharmacy of a hospital while an ADT database may be disposed in the admissions area of a hospital. Alternatively, one or more of the databases of the patient-affiliated data 105 may be disposed external to the facility to which the data pertains.

The patient-affiliated data 105 may be communicatively interconnected to the patient interface device gateway 104 such that information may be transferred: 1) from the patient-affiliated data 105 to the patient interface device gateway 104 and to the master database 113 and the plurality of patient interface devices 101; and 2) from the plurality of patient interface devices 101 through the patient interface device gateway 104 to the master database 113 and to the patient-affiliated data 105. In this regard, the patient interface device gateway 104 may be communicatively interconnected to each database within the patient-affiliated data 105. For example, the patient interface device gateway 104 may be interconnected to the pharmacy database via the network 103 which may be in the form of a Local Area Network (LAN), an intranet, the Internet and/or any other appropriate type of network. The connection between the patient interface device gateway 104 and various components of the patient-affiliated data 105 may be wired or wireless.

As new patients are admitted to a facility, and as patients' conditions change, it may be necessary to update the patient-affiliated data 105. Such updates may be achieved in several different ways. For example, the data within the patient-affiliated data 105 may be updated by entering new information into one of the databases of the patient-affiliated data 105, such as by an admissions clerk upon admitting a new patient or by a pharmacist entering a new prescription into a pharmacy database.

In another example, a user may enter the update information into any one of the plurality of patient interface devices 101. In this regard, a patient interface device, such as patient interface device 101a, may be used to assist in admitting a new patient (e.g., in an emergency room) or in updating information regarding an existing patient. The information may then be transferred to the master database 113 and/or patient-affiliated data 105 via the patient interface device gateway 104. Such a transfer may happen automatically, in that once the data is entered into the patient interface device 101a, it may be transferred to the patient-affiliated data 105 without any other user input or command. In a variation, the user may be prompted by the patient interface device 101a to confirm sending data to the patient interface device gateway 104 and/or patient-affiliated data 105. In still another example, the patient interface device 101a may automatically send information to the patient interface device gateway 104 at the occurrence of a specific event, such as the beginning of delivering a medication to a patient, the reaching of a predetermined milestone during an infusion process (e.g., when half of the infusion has been completed), and/or the completion of the delivery of medication to the patient by the infusion pump 101a.

The patient interface device gateway 104 may update the master database 113 and/or the patient-affiliated data 105. The patient interface devices 101 may also notify the patient interface device gateway 104 if no events have happened over a predetermined period of time. In this regard, such reporting may inform the master database 113 that such patient interface devices 101 are still connected to the network 102 and that such patient interface devices 101 have no new information to be submitted to the master database 113. Relatedly, a lack of such reporting may indicate to the master database 113 that a patient interface device is missing or inoperative. Patient interface devices 101 may also report their position (e.g., location within a facility) to the master database 113. Such position determination may be achieved through any appropriate means. For example, patient interface device location may be determined using network attributes. In another example, patient interface device location may be determined by reference to a known location of a patient receiving care from the patient interface device.

The information sent from the patient interface devices 101 to the patient interface device gateway 104 may contain several different types of information that are desired to be sent to several different places. For example where the patient interface device is an infusion pump, information sent from the patient interface devices 101 may include pump related data (e.g., number of strokes performed, pump serial number) to be sent to a pump surveillance database 107, medication usage data (e.g., a dose of medicine was used) to be sent to a pharmacy database, and patient information (e.g., the dose was administered to a patient) to be sent to a MARs database. The patient interface device gateway 104 may possess the ability to receive such information from the patient interface devices 101 and parse the information and pass the parsed information onto the desired destinations.

The therapy database 106 may contain one or more formularies, medication-specific datasets or therapy-specific data sets. The medication-specific datasets may include medication-specific identification data (e.g., lists of medications approved by a facility) and medication-specific formulation data (e.g., formulas for compounding medical fluids used to deliver medications). The medication-specific data sets may include medication-specific infusion data such as data related to how particular medications may be infused into a patient (e.g., concentrations, flow rates). The therapy database 106 may include and/or be part of a Clinical Decision Support (CDS) system.

As new medications are approved by the facility or as new treatment protocols are introduced for existing medications in the therapy database 106, it may be necessary to update the therapy database 106. Such updates may be achieved in several different ways. For example, the data within the therapy database 106 may be updated by entering new information into one of the datasets of the therapy database 106, such as by a pharmacist under the direction of a Director of Pharmacy entering a new type of drug into a dataset including medication-specific identification data.

In another example, a physician may enter updated information regarding a new treatment protocol for a particular medication into any one of the plurality of patient interface devices 101. The information may then be transferred to the master database 113 and/or the therapy database 106 via the patient interface device gateway 104. Such a transfer may happen automatically, in that once the data is entered into the patient interface device 101a, it may be transferred to the master database 113 and/or the therapy database 106 without any other user input or command.

According to another example of how the therapy database 106 may be updated, the facility may subscribe to a global therapy database 110. The global therapy database 110 may be interconnected to the therapy database 106 via a network, such as via the Internet. The global therapy database 110 may be maintained by a third party and as new therapies and/or medications are added or new administration protocols are developed, the new global therapy database 110 may be updated and the changes pushed to the therapy database 106 and/or the master database 113, thus updating the therapy database 106 and/or the master database 113.

As noted above, the avatar 108 may be capable of constructing patient-specific guidance data sets 109 from information disposed in the database 114. Such constructing may occur automatically when identification information regarding a particular patient and/or a particular dose of medication is inputted into the patient interface device 101a. In this regard, the patient-specific guidance data set 109 for a particular patient will be created locally (e.g., within the patient interface device 101a) on demand.

Accordingly, each patient interface device of the plurality of patient interface devices 101 may contain the information necessary to produce patient-specific guidance data sets 109 for each patient in the patient group 112. For example, for each patient, each patient interface device of the plurality of patient interface devices 101 may include identification data, medication data, and/or treatment data. The medication data may include a list of medications along with rules for determining infusion parameters for a patient. The treatment data may contain specific instructions for use with specific patients (e.g., medications prescribed for each patient in the patient group 112). In this regard, each patient interface device of the plurality of patient interface devices 101 may possess the ability to generate patient-specific guidance data sets 109 for any patient. For example, each patient interface device of the plurality of patient interface devices 101 may possess the ability to generate infusion parameters for a patient. Such infusion parameters may include infusion rate (e.g., mL/hr), infusion duration, dose duration, dose interval, bolus size, or any other appropriate parameter. The infusion parameters may include maximum and/or minimum values for each parameter.

Thus, each patient interface device of the plurality of patient interface devices 101 may be capable of interfacing with any patient in the patient group 112. Thus, any patient interface device of the plurality of patient interface devices 101 may be used to interface with (e.g., infuse liquid medication where the patient interface device is an infusion pump) any patient in the patient group 112 by generating the particular patient-specific guidance data set to be used. In this regard, managing patient interface device inventory is simplified as no searching is needed for a particular patient interface device of the plurality of patient interface devices 101 that contains unique information for a particular patient to be treated.

In an alternative arrangement, the avatars 108 may construct patient-specific guidance data sets 109 for all appropriate patients who have data within the database 114 upon the arrival of such data into the database 114. Moreover, when the database 114 is updated, new patient-specific guidance data sets 109 may be calculated based on the updated data. In this regard, updates to the patient-specific guidance data sets 109 may be triggered by a change to the master database 113. The patient interface device gateway 104 may assist in constructing the master database 113 by accessing the patient-affiliated data 105 and the therapy database 106 via the network 103. For each patient in the patient group 112, the patient interface device gateway 104 may access the patient-affiliated data 105 to obtain information pertinent to the treatment (e.g., medication administration) and/or monitoring for that patient, such as current drug prescriptions, patient condition, patient health history, patient weight, patient age, patient gender, known drug allergies, other drugs being administered, and/or any other appropriate data. The patient interface device gateway 104 may access the therapy database 106 to obtain, for example, medication formulation data and/or medication infusion data for the particular medications prescribed to the patient. This process may be repeated for each patient of the patient group 112 resulting in the construction of the master database 113.

The avatar 108 may also construct or update a patient-specific guidance data set 109 for a particular patient in response to the entering of new data into a patient interface device of the plurality of patient interface devices 101. Such construction or updating may be automatic. The new data entered may be appropriate for storage within the patient-affiliated data 105 and/or the therapy database 106. As such, the new data may be forwarded, via the patient interface device gateway 104 and network 103, to the patient-affiliated data 105 and/or the therapy database 106 and the patient-affiliated data 105 and/or the therapy database 106 may be updated accordingly. The master database 113 may also be updated and in turn the databases 114 in each of the other patient interface devices 101 may be updated in response to the updates to the master database 113.

As noted, the patient interface device gateway 104 may facilitate the maintenance of the master database 113. In this regard, updates or changes to the patient-affiliated data 105, the therapy database 106, or any other source used to populate the master database 113 may, through the patient interface device gateway 104, be incorporated into the master database 113. Such changes may occur, for example, when a new patient is admitted, when a patient's information changes, when a new medication is added, or when a formulation for an existing medication is changed. Such incorporation of changes may, for example, occur as a result of the patient interface device gateway 104 periodically accessing the various interconnected databases to determine changes that may have occurred to the various interconnected databases. An exemplary way of checking for such changes would be to transfer the entirety of the various interconnected databases and compare the information to the master database 113 to determine changes. An alternative process may be to query the various interconnected databases for changes that may have occurred since the last query and only incorporate the recent changes into the master database 113. Still another alternative is for the external databases to be configured to notify the patient interface device gateway 104 when a change occurs.

As previously noted, any changes to the master database 113 may be communicated to the database 114 of each avatar 108. Such communication may take any appropriate form. In a first example, the database 114 of each avatar 108 may be updated by copying an entirety of the master database 113 to each database 114 of each avatar 108. In a second example, only changed records (e.g., a complete patient record for a particular patient that has changed) may be sent to each database 114 of the patient interface devices 101. In a third example, only changed data (e.g., an update to a patient's condition, but not other patient information in the patient's record that is unchanged) may be sent to each database 114 of the patient interface devices 101.

The patient interface device gateway 104 may be in the form of a software program resident on a computer system. The master database 113 may be resident on the same computer system as the patient interface device gateway 104 or it may be resident on a separate device. Where the master database 113 is resident on a separate device, as illustrated in FIG. 1A, that device may be interconnected directly to the patient interface device gateway 104 or it may be communicatively interconnected to the patient interface device gateway 104 through the network 103.

Each patient interface device of the plurality of patient interface devices 101 may contain an independent avatar 108. In such an embodiment, any updates to the patient-affiliated data 105 and/or therapy database 106 may be communicated to the master database 113 via the patient interface device gateway 104 and then communicated to each individual avatar 108 via the patient interface device gateway 104, which may in turn update each currently used individual patient-specific guidance data set 109 that may change as a result of the update.

The logic 115 of the avatar 108 and therefore the set of rules it uses to create and update the patient-specific guidance data sets 109 may be derived from one or more of a plurality of different sources. For example, regulatory rules, industry rules, health care provider rules, individual facility rules, physician preferences and patient preferences may all be used to determine the configuration of the logic 115.

When a source for the logic 115 is updated, the logic 115 may be correspondingly updated. For example, such an update may be entered into the patient interface device gateway 104 and then be sent from the patient interface device gateway 104 to each patient interface device of the plurality of patient interface devices 101 over the network 102. In this regard, each avatar 108 of the system 100 may be maintained. A master copy of an avatar may be maintained, for example, in the master database 113.

Each patient interface device of the plurality of patient interface devices 101 may be a device capable of controlling the flow rate of medications being delivered to a patient, controlling the delivery of therapy to a patient, and/or controlling the monitoring of one or more patient attributes. Such control may be achieved using a microprocessor and appropriate software and/or hardware disposed within each patient interface device of the plurality of patient interface devices 101. Each patient interface device of the plurality of patient interface devices 101 may further include memory 119 where the patient-specific guidance data sets 109 may be stored. Where the avatar 108 is disposed within each patient interface device, the memory may also store the avatar 108.

Each patient interface device may include one or more components or inputs for the input of data into the patient interface device. Such components may be in any appropriate form, such as for example, buttons, keypads, keyboards, touch screens, barcode readers, radio frequency identification (RFID) tag readers, biometric readers, card readers, data ports, network interconnections, wireless network interfaces and/or any other appropriate form. The types of data that may be received by the patient interface device include, but are not limited to, patient identification data, caregiver identification data, patient-specific attributes, medication identification data, medication-specific attributes, patient-specific guidance data sets and patient status data. Each patient interface device may include ports operable to be interconnected to devices or sensors that are operable to measure and/or monitor various patient attributes such as, for example, heart rate, temperature, blood pressure, and oxygen saturation of blood.

Each patient interface device of the plurality of patient interface devices 101 may include a plurality of outputs. Where the patient interface device is an infusion pump, a first output may be a mechanical output operable to pump medication through tubing to a patient. For example, the patient interface device may include a movable ram operable to interface with and move a plunger of a syringe to cause medication to be expelled from the syringe. The ram may be controllable to deliver a medication to a patient at a precisely controlled rate according to the patient-specific guidance data set for the patient. In another implementation of the patient interface device as an infusion pump, the mechanical output may be used to drive a peristaltic pump. The mechanical output of the patient interface device may be driven by a drive (e.g., a motor) and the patient interface device may include logic (e.g., a motor controller) and one or more sensors that are used to produce a controlled motion of the drive to produce a controlled flow rate of medication to a patient.

Other outputs that a patient interface device may generally comprise may include a video display which may, for example, communicate information related to the patient, infusion status and parameters, patient attributes, medication, patient interface device performance, medical personnel, or any other appropriate subject. The patient interface device may also include an audio output capable of sounding an alarm in response to predetermined occurrences (e.g., attempting to load an incorrect medication onto the patient interface device, unsatisfactory signal from a sensor measuring an attribute of the patient). The patient interface device may also have the capability to send alerts of such occurrences to a variety of places via a network connection (e.g., a wireless network connection). Such alerts may be sent to individuals (e.g., nurses and/or physicians) or to locations (e.g., a nursing station). The audio output may also be capable of playing audio operation instructions to assist in operating the patient interface device.

The network 102 connection may be of any appropriate form for exchanging data between devices and may interconnect the plurality of patient interface devices 101 to the patient interface device gateway 104. The patient interface device gateway 104 may, in turn, be interconnected via network 103 to the patient-affiliated data 105, the therapy database 106, the pump surveillance database 107, other facility databases, and to databases external to the system 100, such as the global therapy database 110 and the global master pump surveillance database 111. The networks 102, 103 may be independent networks as illustrated in FIG. 1A, or alternatively network 102 and network 103 may be the same network. For example, network 102 and network 103 may be a facility's existing LAN. In such an example, the patient interface device gateway 104 may communicate with the plurality of patient interface devices 101 through the LAN as well as communicate with the databases (patient-affiliated data 105, therapy database 106, pump surveillance database 107, databases external to the system 100) through the LAN.

As noted, the patient interface device gateway 104 may be in the form of or resident on a computer system. The interconnections between the patient interface device gateway 104 and the patient-affiliated data 105, the therapy database 106, and to the pump surveillance database 107, may all be through a facility's existing network and/or through a dedicated network for the system 100. It is also noted that the patient-affiliated data 105 may be disposed across many individual computer systems. For example, the pharmacy database may be disposed on a computer system within the pharmacy of the facility, while the database that contains the ADT information may be located elsewhere in the facility. However, both the pharmacy database and the ADT database may be interconnected to the facility's LAN and thus in communication with the patient interface device gateway 104.

The pump surveillance database 107 may contain data related to the performance of each patient interface device of the plurality of patient interface devices 101 that is in the form of or includes an infusion pump. In this regard, as the patient interface devices 101 in the form of infusion pumps are operated to deliver medications to patients, each such patient interface device may create logs of its activity. Such logs may contain data such as start and finish times of performed infusions, number of strokes performed, total running time, type of medication delivered, and any other appropriate data that may affect or indicate performance of the patient interface devices 100. The patient interface devices 101 may send such logs to the patient interface device gateway 104, which may then send the logs to the pump surveillance database 107 via the network 103. In turn, the data within the pump surveillance database 107 may be monitored and analyzed to assist in determining, for example, maintenance tasks to be completed for particular patient interface devices and/or replacement of particular patient interface devices. Additionally, data within the pump surveillance database 107 may be automatically periodically delivered to the global master pump surveillance database 111. The global master pump surveillance database 111 may aggregate patient interface device performance data from a plurality of facilities to, for example, further refine maintenance and replacement schedules and determine potential failure modes.

Other databases for storing performance data related to other types of patient interface devices 100 may also be interconnected to the patient interface device gateway 104 through the network 103. For example, a blood pressure sensor monitor database and/or a compression device monitor database may be interconnected to the patient interface device gateway 104 through the network 103. Such databases may function similarly to the pump surveillance database 107 described above and may be used in a similar manner to manage the patient interface devices 101. Moreover, global databases, similar to the global master pump surveillance database 111 may exist for these other types of patient interface devices 109.

The data described herein as being transferred between the patient interface device gateway 104 and the patient interface devices 101 may be encrypted. Moreover, data being transferred between individual patient interface devices of the plurality of patient interface devices 101 and/or between avatars 108 and/or between avatars 108 and patient interface devices 101 may be encrypted. Such encryption may help to maintain security of medical data associated with patients as it is transmitted from point to point. Such encryption may assist in preventing unauthorized altering of data and thus help to maintain patient safety. Furthermore, such encryption may assist in preventing unauthorized accessing of data and thus help to maintain patient privacy.

The data described herein as being stored in the databases 114 and/or the master database 113 may be encrypted. As with data being transmitted, such encryption may help to maintain security of medical data stored within the system 100, thus protecting safety and privacy.

The maximum predetermined amount of time between when data is entered into an external database (e.g., patient-affiliated data 105) and when the entered data is distributed to the master database 113 may be any appropriate amount of time. For example, such a maximum predetermined time may be on the order of one second, one minute, one or more hours, or any appropriate time therebetween. The maximum predetermined time may be selectable by, for example, a system administrator and may be based on safety requirements, bandwidth of the network 103, the amount of data to be transferred, and/or other appropriate factors. In an arrangement, at intervals equal to the selected maximum predetermined time, the patient interface device gateway 104 may query the various interconnected databases for changes that have occurred since the last query.

In an alternative arrangement, the master database 113 may be at least partially maintained in real-time or near real-time. In such an embodiment, when changes are made to an external database (e.g., patient-affiliated data 105), the external database may be configured to notify the patient interface device gateway 104 of the changes. In this regard, the patient interface device gateway 104 may subscribe to some or all of the external databases and thus be informed when changes to those databases occur. The system 100 may utilize a combination of update methods where some databases must be queried while other databases notify the patient interface device gateway 104 when changes have occurred.

Similarly, the patient interface devices 101 may be configured such that changes to one of the databases 114 within a patient interface device may be immediately communicated to the patient interface device gateway 104, which may then immediately pass the update to the master database 113. Alternatively, the patient interface devices 101 may be configured to send updates of their databases 114 at regular intervals. Each patient interface device may also be configured to send notices to the patient interface device gateway 104 if no changes to its database 114 have occurred for a predetermined period of time.

The master database 113 may communicate regularly to the plurality of patient interface devices 101. In this regard, at regular time intervals, the master database 113 may broadcast a journal to every patient interface device of the plurality of patient interface devices 101. Such journals may contain any updates that were made to the master database 113 since the last journal was broadcast. In this regard, upon receipt and incorporation of a journal entry, the patient interface devices 104 may have knowledge that their corresponding databases 114 were up to date as of the time of such incorporation. The journals may be sequentially numbered such that any patient interface device, upon receiving a journal broadcast, will be able to determine from the serial number if any journal broadcasts were missed. For example, if a patient interface device receives journal number 1004 and the last journal received by the patient interface device was journal number 1002, the patient interface device may determine that it has missed journal number 1003. The patient interface device may then request journal number 1003 before applying the changes of journal number 1004.

If no data updates to the master database 113 occur over a predetermined period of time, the master database 113 may inform the patient interface devices 101 as such in a journal that contains no updated data. Thus, the patient interface devices 104 may have knowledge that their databases 114 were up to date as on the receipt of such an empty journal entry.

In this regard, each database 114 of each patient interface device of the plurality of patient interface devices 101 may be maintained such that the data therein reflects all but the most recent changes to other databases 114 of other patient interface devices 101 and to external databases. For example, where the patient interface devices 101 notify the patient interface device gateway 104 of changes to its databases 114 every minute, and where the master database interrogates external databases every minute, and where the master database 113 broadcasts a journal every minute, any data changes within the system 100 will be reflected in the databases 114 of the patient interface devices 101 within at most about two minutes (e.g., one minute for a patient-affiliated data 105 change to be recorded in the master database 113 plus one minute until a journal broadcast is sent out).

The above-described data maintenance arrangements may support additional system features. For example, if a failure occurs in network 102 and/or network 103, the individual patient interface devices 101 may be capable of tracking the amount of time that passes from the last contact (e.g., the time of the last received journal) with the patient interface device gateway 104. The patient interface devices 101 may be programmed to remain operational for a predetermined amount of time from receiving a last-in-time update. For example, in an arrangement, the system 100 may be configured such that updates (e.g., journals) are sent to the databases 114 every five minutes and the individual patient interface devices 101 may be configured such that they may remain operational for up to an hour after receiving a last-in-time update. Thus, in such a case, if the network 102 becomes non-operational, the patient interface devices 101 will remain operational for up to one hour. The length of one hour is exemplary. The actual length used by a system 100 may be shorter or longer and may also be programmable (e.g., by hospital administrators). Such operation may be used to prevent the use of "stale" data by a patient interface device 101. "Stale" data, as used herein, indicates data that has not been updated for a predetermined amount of time and as a consequence may be undesirable for use in controlling the operation of a patient interface device 101.

Once information within the avatar 108 is determined to be stale, the avatar 108 may prevent usage of the stale data to operate the patient interface device 101. Such prevention may be in any appropriate form. For example, the avatar 108 may lock out users and only allow access to the data (e.g., the database 114 and/or the patient-specific guidance data set 109) by system administrators or other designated personnel. In this regard, data that is only resident in the database 114 and nowhere else (e.g., data related to an infusion that occurred after the last in time communication with the patient interface device gateway 104) may be retrieved and incorporated into the master database 113.

In another example, if the avatar 108 determines that the data has been stale for a predetermined amount of time (e.g., several hours or days), it may wipe (e.g., delete such that the deleted data is unrecoverable) the memory that contains the stale data (e.g., the memory that contains the database 114 and/or the patient-specific guidance data set 109). Such wiping may optionally exclude any information within the database 114 that has not been communicated to the patient interface device gateway 104. Such action would prevent use of the data to run the patient interface device 101 and would also help data security by limiting or preventing unauthorized access to the data. Since the patient interface devices 101 may be relatively small, wireless units (e.g., portable infusion pumps), they may be susceptible to theft or unintentional removal from the facility. Accordingly, the ability to wipe the memory that contains stale data may be of particular value to data security.

When the networks 102 and/or 103 are restored after a period of unavailability, the patient interface devices 101 may send any data to the patient interface device gateway 104 that had not been previously sent, such as, for example, data related to infusions that were performed by the patient interface devices 101 while the networks 102 and/or 103 were unavailable. The master database 113 may then be updated accordingly. Additionally, if the network 103 was unavailable, any changes that occurred to the external databases (e.g., patient-affiliated data 105, therapy database 106) may be communicated to the master database 113. Once the master database 113 has been fully updated, each individual database 114 in the patient interface devices 101 may be correspondingly updated.

Figure 1B:
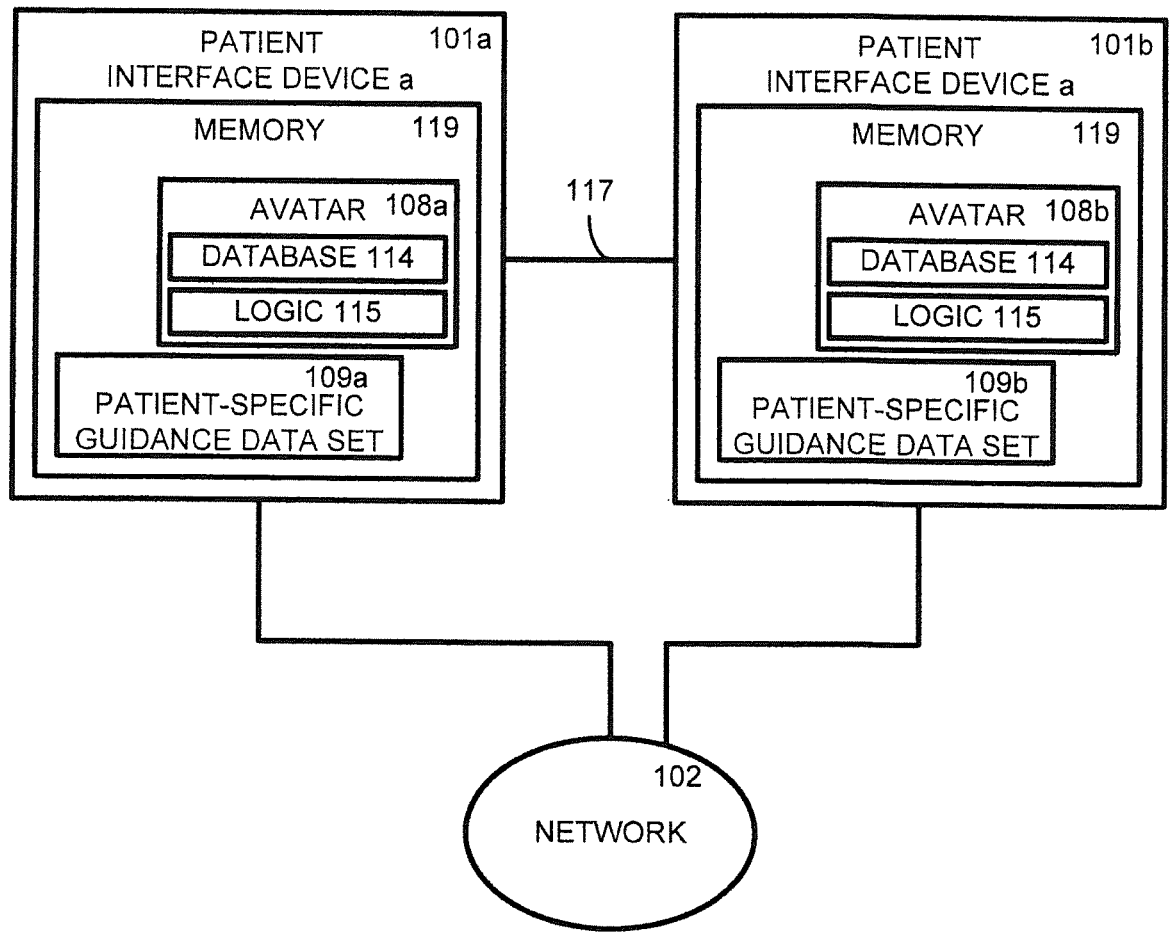
FIG. 1B illustrates a portion of the system of FIG. 1A with an interconnection between patient interface devices.

In an implementation of the system 100, a single avatar may control more than one patient interface device 101. Such an implementation is illustrated in FIG. 1B. In FIG. 1B, the patient interface device 101a and patient interface device 101b are directly connected via link 117. Both devices 101a, 101b may be located proximate to a patient (e.g., bedside). Both patient interface device 101a and patient interface device 101b may be interconnected to the patient. For example, patient interface device 101a may be in the form of a first infusion pump and patient interface device 101b may be in the form of a second infusion pump, where each patient interface device 101a, 101b is used to deliver a different medical liquid to the same patient.

Link 117 may be of any appropriate form, including for example, a wireless link (e.g., Wi-Fi and/or Bluetooth), a direct wired connection, or a fiber optic link. The link 117 may be resilient in that it may be capable of remaining operational despite interference that may be present in the facility. When linked, one of the avatars, for example avatar 108a, may become a master avatar, while the other avatar, for example avatar 108b, may become a slave avatar or become dormant while the master avatar 108a controls the slave patient interface device 101b. Which avatar becomes the master and which avatars or patient interface devices become the slaves may be determined automatically upon direct interconnection (e.g., by selecting the master to be the unit with the highest serial number) or a user may select which avatar is the master.

In such a master-slave relationship, the master avatar 108a may provide the slave patient interface device 101b with the patient-specific guidance data set 109b. Thus, using patient-specific guidance data sets 109a and 109b, master avatar 108a may control both patient interface device 101a and patient interface device 101b. Where both patient interface devices 101a and 101b are administering medication, the use of the master avatar 108a to control both patient interface devices 101a, 101b may enhance the ability of the system to prevent the administration of drugs or dosages by the individual patient interface devices 101a, 101b that are incompatible with each other. The master avatar 108a may handle all communications with the patient interface device gateway 104.

In another example, patient interface device 101a may be in the form of a patient monitor and patient interface device 101b may be in the form of an infusion pump. The avatar 108a may serve as a master avatar and control both the patient monitor patient interface device 101a and the infusion pump patient interface device 101b. In such a configuration, the avatar 108a may control the infusion pump patient interface device 101b based on feedback from the patient monitor patient interface device 101a. For example, where the patient monitor patient interface device 101a is a heart rate monitor, the delivery of medication via the infusion pump patient interface device 101b may be altered (e.g., stopped) in response to a change in patient heart rate detected through the heart rate monitor. Any such required alterations may be recorded in the database 114 of patient interface device 101a and communicated to the patient interface device gateway 104 and master database 113 (and then to all other patient interface device databases 114).

Figure 1C:
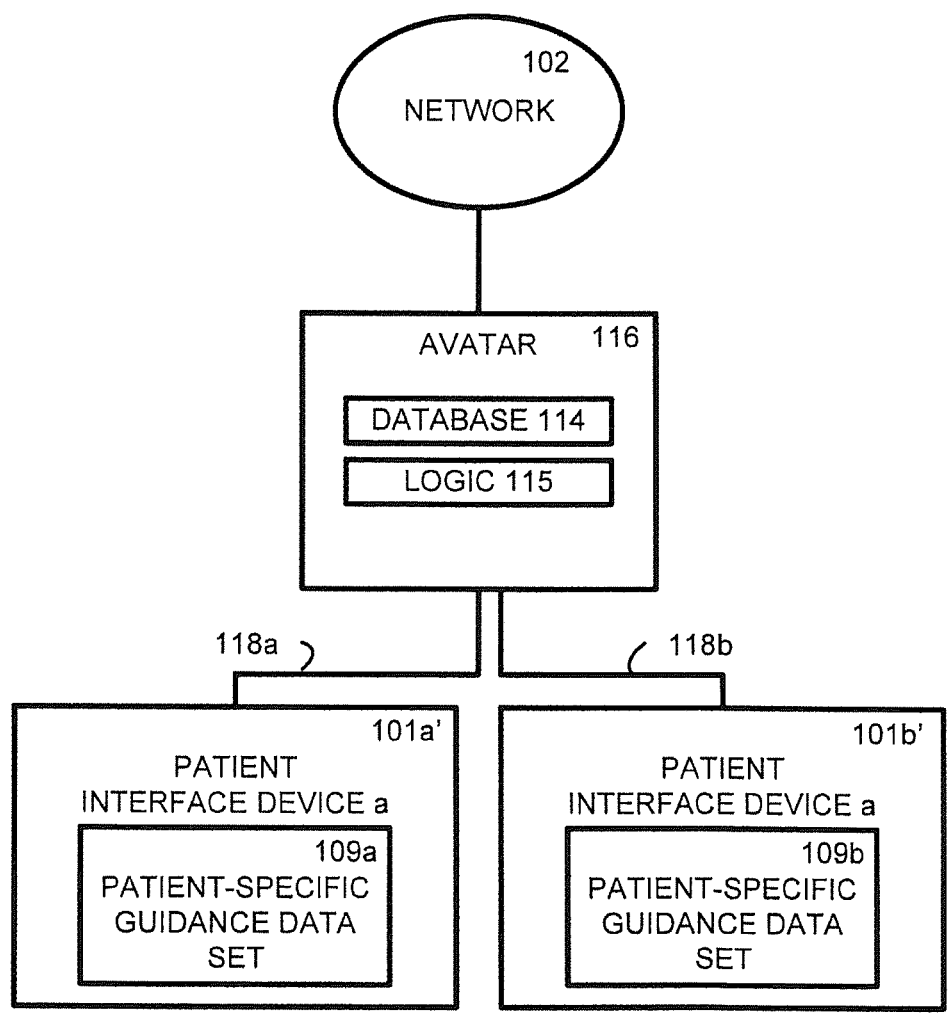
FIG. 1C illustrates a portion of the system of FIG. 1A with an avatar external to the patient interface devices.

In a variation of the system 100, at least a portion of the avatars may be devices separate from the patient interface devices 101. In such a variation, the avatars may act as parent devices controlling one or more child patient interface devices. FIG. 1C illustrates such a configuration where avatar 116 is a stand-alone device communicatively interconnected to patient interface device 101a' and 101b'. Communications to the patient interface device gateway 104 would be managed by the avatar 116 which may be interconnected to the network 102. Using the logic 115, the avatar 116 may generate patient-specific guidance data set 109a and patient-specific guidance data set 109b based on data within the database 114, and then transfer the patient-specific guidance data set 109a and patient-specific guidance data set 109b to the patient interface devices 101a' and 101b', respectively.

The communication between the patient interface devices 101a' and 101b' may be one way (e.g., the patient interface devices 101a' and 101b' may accept a program for operation from the avatar 116, but may not provide any operational feedback) or two way (e.g., the 101a' and 101b' may provide operational feedback). The links 118a and 118b between the avatar 116 and the patient interface devices 101a' and 101b' may be of any appropriate form, including for example, a wireless link, a direct wired connection, or a fiber optic link. The link between the avatar 116 and the patient interface devices 101a' and 101b' may be a resilient, highly reliable link that does not require network 102 or network 103 to be operational. In this regard, the avatar 116 and patient interface devices 101a' and 101b' may remain operational independent of whether network 102 or network 103 are operational. Thus, as long as the database 114 does not contain stale data, the patient interface devices 101a' and 101b' may remain operational and interface with a patient.

The avatar 116 may take any appropriate form including a hand held device, such as a smart phone or tablet computer that personnel may move from room to room. In another example, the avatar 116 may be a stationary device such as a personal computer or workstation located in a room.

Figure 2:
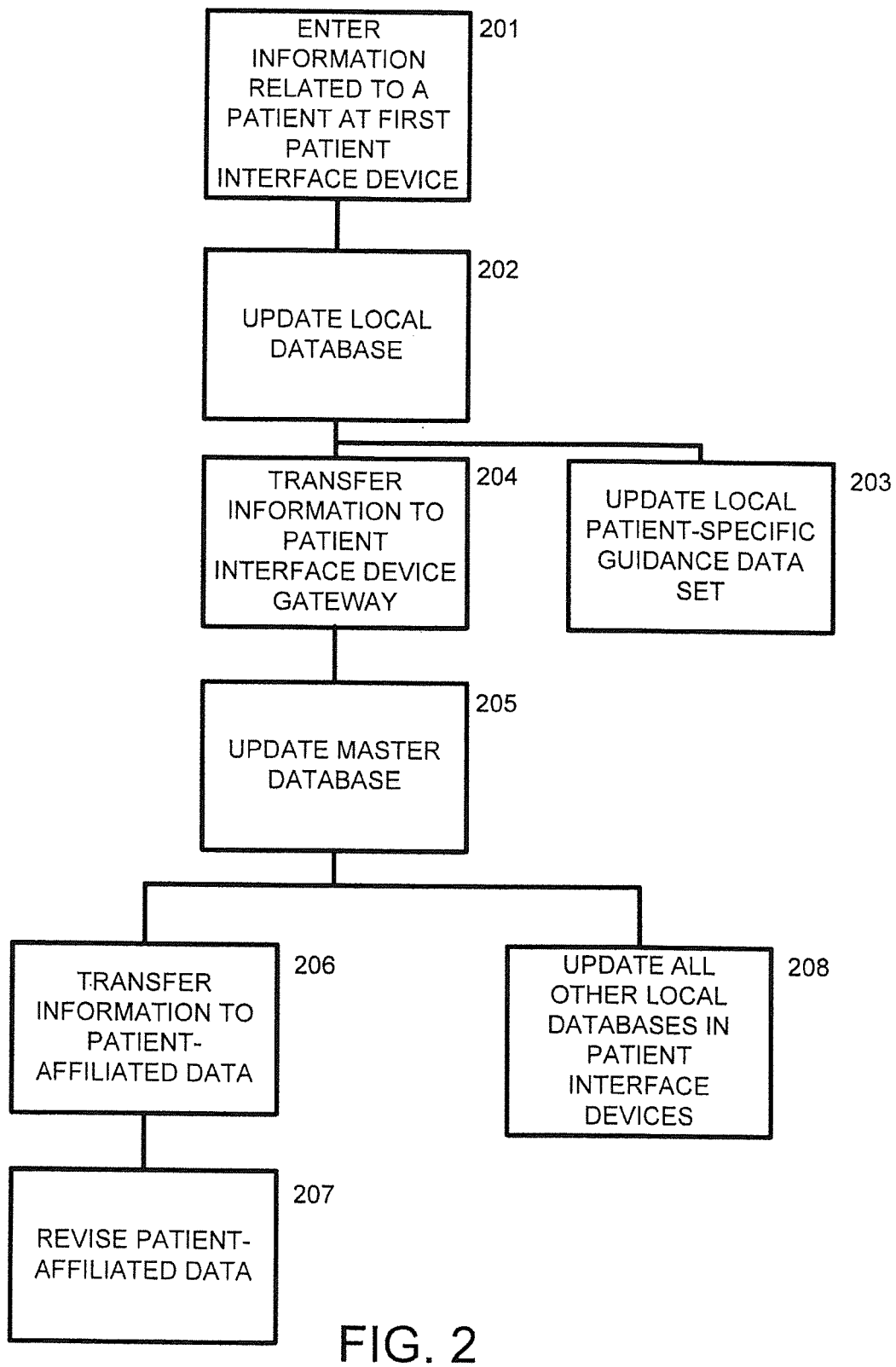
FIG. 2 is a flowchart of a method of updating a patient-specific guidance data set related to a patient by inputting data into a patient interface device.

FIG. 2 is a flowchart of a method of updating a patient-specific guidance data set related to a patient, where the patient-specific guidance data set is adapted for use by a patient interface device (e.g., for use in infusion pump administration of at least one medication to a corresponding patient). The method also includes updating all databases resident within avatars and updating the patient-affiliated data.

The first step 201 may be to enter information related to a patient into a first patient interface device. The information related to the patient may include information that makes it preferable to update the patient-specific guidance data set for the patient, such as an update as to the patient's condition. The second step 202 may be to update the database of the avatar associated with the patient interface device. A next step 203 may be to update the patient-specific guidance data set based on the newly entered data. Step 203 may be performed by the avatar associated with the patient interface device. A next step 204 may be to automatically transfer at least a portion of the information from the first patient interface device to the patient interface device gateway. Step 204 may be performed in response to the first step 201 and over a communication link, such as a network connection. A following step 205 may then be to update the master database. Additional steps 206, 207 may include transferring the information from the master database via the patient interface device gateway to one or more sources of patient-affiliated data to create revised patient-affiliated data.

Another step 208, may be to automatically update other databases in other patient interface devices such that each patient interface device may be capable of generating an appropriate patient-specific guidance data set if required. Thus, each patient interface device (the first patient interface device and each patient interface device of the plurality of other patient interface devices) may have stored in its database the information necessary to generate any appropriate patient-specific control data.

The method of FIG. 2 may further include accessing, after step 203, the updated patient-specific guidance data set related to the patient, and interfacing with (e.g., infusing medication into) the patient according to the patient-specific guidance data set related to the patient.

As illustrated, the method of FIG. 2 was triggered by step 201 when information related to a patient was entered into a first patient device. The method may also be triggered by the patient interface device interfacing with the patient. For example, where the patient interface device is an infusion pump, step 201 may be replaced with the step of infusing medication into the patient and the subsequent generation of information related to the infusion (e.g., amount of infusion, duration of infusion, time of infusion). In this regard, the information referenced in subsequent steps would be the information related to the infusion.

In a variation of the method of FIG. 2, the identity of a patient may be unknown (e.g., where a patient arrives in an emergency room without the ability to be identified). In such a case, only information that is available may be entered at step 201. Such information may include gender, approximate height and weight, approximate age, and information regarding patient condition. The remainder of the method may then be executed in a manner similar to as discussed above.

In another variation of the method of FIG. 2, where the patient interface device is an infusion pump, the identity of a patient may be unknown and the patient interface device operator may simply scan a medication and manually enter an infusion rate and then instruct the patient interface device to carry out the infusion. In such a scenario, the patient interface device may be operable to sound an alarm if the patient interface device operator enters in parameters that are considered to be dangerous.

FIG. 3 is a flowchart of a method of updating a patient-specific guidance data set related to a patient based on an update to the patient-affiliated data. The first step 301 may be to revise a patient-affiliated database with information related to the patient to create an updated patient-affiliated database. The information related to the patient may include information, such as a change in medication prescribed to the patient or the condition of the patient that makes it preferable to update the patient-specific guidance data set for the patient. The second step 302 may be to automatically communicate the revision to the patient interface device gateway, followed by the step 303 of updating the master database. As noted above, this may be performed by the patient interface device gateway periodically downloading all or part of the patient-affiliated data to the master database, or by the patient-affiliated data notifying the patient interface device gateway when a change has occurred. After the master database has been updated, the master database may be used in step 304 to update the databases resident in each avatar. Such updating may occur on a periodic basis or the updating may be triggered by a change to the master database. The updating of the databases may be performed by replacing the entirety of each of the databases or it may be performed by transferring only selected (e.g., changed) data to the databases.

A next step 305 may be to automatically create an updated patient-specific guidance data set at a patient interface device that has been associated with a particular patient. In the next step 306, the updated patient-specific guidance data set may be stored in the patient interface device. For example, where a patient interface device had previously created a patient-specific guidance data set for use in interfacing with a patient, the receiving of an update to the patient interface devices database may cause the patient interface device to create the updated patient-specific guidance data set. In a more specific example where the patient interface device is an infusion pump, the infusion pump may have previously run an infusion for a patient using a particular set of parameters (e.g., flow rate, infusion duration). The change to the patient-affiliated data (step 301) may result in it being desirable to alter the infusion parameters for the patient. In this regard, following the current method would result in an updated patient-specific guidance data set that includes updated infusion pump parameters being stored at the infusion pump.

The entire process illustrated in FIG. 3 may occur automatically (e.g., with no further human interaction after step 301) in response to the revision of the patient-affiliated data.

FIG. 4 is a flowchart of a method of updating a patient-specific guidance data set related to a patient based on an update to the therapy database. The method of FIG. 4 is similar to the method of FIG. 3, with a difference being that the updating in method of FIG. 3 is triggered by an update to the patient-affiliated database, whereas the updating in method of FIG. 4 is triggered by an update to the therapy database. Accordingly, the first step 401 of the method may be to revise a therapy database with information related to a therapy and/or medication to create a revised therapy database. The information related to the medication may include information, such as a new injection protocol, that makes it preferable to update the patient-specific guidance data set for the patient. The second step 402 may be to automatically communicate the revision to the patient interface device gateway, followed by the step 403 of updating the master database. After the master database has been updated, the master database may be used in step 404 to update the databases resident in each avatar.

A next step 405 may be to automatically create an updated patient-specific guidance data set at a patient interface device that has been associated with a particular patient. In the next step 406, the updated patient-specific guidance data set may be stored in the patient interface device.

Exemplary applications of the above systems and methods will now be presented.

A hospital may maintain a plurality of different databases related to its patients. In this regard, the hospital may have a pharmacy database maintained by an on-site pharmacy that contains data related to medication prescribed for patients. The hospital may maintain a general medical record database, a MAR database, an ADT database, and other databases that contain information related to specific patients. Together, these databases may form the patient-affiliated data 105.

The hospital may also maintain data related to medications and their delivery. Such data may be in the form of formularies that list medications approved for use in the hospital, along with formulation data for mixing the medications and dosage information for administering the medications. The data may also include infusion parameters and/or formulas for the medications that may be administered through infusion. Together this data may form the therapy database 106. The hospital may also subscribe to the global therapy database 110. The global therapy database 110 may be maintained by a third party and updates to the global therapy database 110 may be communicated to the therapy database 106 at regular intervals and/or when the global therapy database 110 updates medications and/or therapies administered by the hospital. The therapy database 106 may also include custom formularies not present in the global therapy database 110.

The hospital may also include the plurality of patient interface devices 101. The networks 102, 103 and the patient interface device gateway 104 may communicatively interconnect the patient-affiliated data 105 and the therapy database 106 with the plurality of patient interface devices 101.

When a first patient is admitted to the hospital, the hospital may update the patient-affiliated data 105 with the first patient's information. This may include identification data, data related to the first patient's condition, and prescribed medication data.

The pertinent information from the patient-affiliated data 105 related to the first patient may be uploaded to each patient interface device of the plurality of patient interface devices 101 such that the avatar 108 in each patient interface device of the plurality of patient interface devices 101 may be capable of locally constructing the patient-specific guidance data set 109 for the first patient.

Distributed data and avatars may have the advantage that if new patient-affiliated data or new medication data is entered into a particular patient interface device, a new patient-specific guidance data set may be created locally (within an patient interface device) by the local avatar. Thus, the ability to locally develop an updated patient-specific guidance data set may not be dependent on an available network connection.

After the first patient has been admitted, the first patient may be placed in a room with a first patient interface device 101a of the plurality of patient interface devices 101. Where the patient interface device is an infusion pump, a caregiver (e.g., nurse, physician) may then start the process of administering medication to the first patient.

The caregiver may start by entering into the first patient interface device 101a identification data for the caregiver followed by identification data for the patient. This may be achieved in any appropriate manner including the scanning of bar codes associated with the caregiver and patient using a bar code scanner communicatively interconnected to the first patient interface device 101a. Next, the caregiver may enter into the first patient interface device 101a identification data for the medication to be administered. This may also be accomplished by scanning a bar code on the container of the medication. If the medication is not one of the medications approved for use with the first patient an audio and/or visual alarm may be generated by the patient interface device 101a to alert the caregiver of this fact. If the medication is approved for the first patient, the patient interface device 101a may generate a patient-specific control data for the patient and load the appropriate infusion parameters from the patient-specific guidance data set 109 for the first patient. The infusion parameters may include typical infusion parameters such as flow rate and total delivery time. Furthermore, since the patient-specific guidance data set 109 was constructed locally on the first patient interface device 101a, there may be no need for the first patient interface device 101a to engage in network communications to determine if it is permissible to perform the infusion. Thus, during network outages, the first patient interface device 101a may remain operational. Furthermore, there may be little or no delays for network communications between the time the patient and medication identification information is entered into the first patient interface device 101a and when the first patient interface device 101a is ready to perform an infusion.

The caregiver may load the medication onto the first patient interface device 101a, interconnect the output of the patient interface device to the first patient (e.g., through tubing interconnected to a catheter). The caregiver may then start the delivery of the medication using the first patient interface device 101a. The first patient interface device 101a may communicate with the patient interface device gateway 104 to update the master database 113 and patient-affiliated data 105 with information related to the start of the infusion process.

Once the first patient interface device 101*a* completes the infusion process, the first patient interface device 101*a* may communicate with the patient interface device gateway 104 to update the master database 113 and patient-affiliated data 105 with information related to the completion of the infusion process. Such information may include patient, medication, and infusion process information. Thereafter, the avatar 108 may be employed to construct an updated patient-specific guidance data set for the first patient. The updated patient-specific guidance data set may reflect that the first patient received the infusion of medication. Also, the updates to the master database 113 related to the performance of the infusion may be communicated to every other patient interface device such that all patient interface devices have the updated data and would be available for subsequent interfacing with the first patient if required to do so.

The first patient interface device 101*a* may also communicate information regarding pump performance to the patient interface device gateway 104. The patient interface device gateway 104 may forward such information to the pump surveillance database 107 upon completion of the infusion process. The first patient interface device 101*a* may send information regarding non-patient-specific performance of the first patient interface device 101*a*. For example, such information may include start and stop times, total number of strokes, total run time, and any other appropriate data collected by the first patient interface device 101*a* during the infusion.

At a later point in time, a second caregiver, who may be unaware of the first infusion, may attempt to repeat the infusion process. However, upon accessing the updated patient-specific guidance data set for the first patient, the first patient interface device 101*a* may alert the second caregiver that the second infusion is not permitted since the first infusion has already been administered or since it is too close in time to the first infusion to be performing a second infusion. Moreover, since the updated information was uploaded to each patient interface device, if the second caregiver had attempted to repeat the infusion process using a different second patient interface device, the second patient interface device would have issued the same alert to the second caregiver.

After the first infusion is complete, the caregiver may at a later point in time attempt to administer a second medication to the first patient using the first patient interface device 101*a*. In the situation where the second medication is incompatible with the first medication, the first patient interface device 101*a* may alert the caregiver that the second infusion is not compatible with the previously delivered medication. Moreover, since the updated information was uploaded to each patient interface device, if the caregiver, or a second caregiver, had attempted to perform the incompatible infusion using a different second patient interface device, the second patient interface device would have issued the same alert.

While staying at the hospital, the first patient's condition may change. For example, the first patient may develop an additional condition that may require an additional infusion of medication. Under such circumstances, the caregiver may update the patient-affiliated data 105 for the first patient. In a first scenario, the caregiver may enter information related to the additional condition into the first patient interface device 101*a*. The information then may be communicated to the patient-affiliated data 105 via the patient interface device gateway 104. Thereafter, the avatar 108 may be employed to construct an updated patient-specific guidance data set for the first patient. This updated patient-specific guidance data set may reflect that the first patient's condition has changed.

In a second scenario, the caregiver may enter information related to the additional condition directly into the patient-affiliated data 105. For example, the caregiver may enter the information into a terminal of the pharmacy database. Thereafter, the master database 113 may be updated with the information and, in turn, each patient interface device of the plurality of patient interface devices 101 may receive the updated information. Then, the avatar 108 may construct an updated patient-specific guidance data set for the first patient that may reflect that the first patient's condition has changed.

While the first patient is admitted to the hospital, the hospital may decide to change the protocol for delivery of the first medication. In this regard, a caregiver or hospital administrator may revise infusion data within the therapy database 106 related to the delivery of the first medication. For example, the nominal delivery rate of the first medication may be reduced. This revision may be entered into the system at a terminal of the therapy database 106 or at one of the patient interface devices of the plurality of patient interface devices 101. In either case, the master database 113 may be updated with the information and, in turn, each patient interface device of the plurality of patient interface devices 101 may receive the updated information. Thereafter an avatar 108 may be employed to construct an updated patient-specific guidance data set for the first patient that reflects the new protocol.

While the first patient is admitted to the hospital, the third party administrator of the global therapy database 110 may decide to change the protocol for delivery of the first medication. This revision may be communicated to the therapy database 106 to revise infusion data within the therapy database 106 related to the delivery of the first medication. Thereafter, the master database 113 may be updated with the information and, in turn, each patient interface device of the plurality of patient interface devices 101 may receive the updated information. Thereafter, an avatar 108 may be employed to construct an updated patient-specific guidance data set for the first patient that reflects the new protocol. Moreover, updated patient-specific guidance data sets may be generated at other patient interface devices for every other admitted patient of the hospital whose patient-specific guidance data set includes the first medication.

As described, each patient interface device of the plurality of patient interface devices 101 may contain the data necessary to create a patient-specific guidance data set 109 for the first patient. This may be advantageous for additional reasons. For example, if a particular patient interface device of the plurality of patient interface devices 101 experiences a failure, any other patient interface device of the plurality of patient interface devices 101 could be substituted for the failed patient interface device since each one would contain the data necessary to create an appropriate patient-specific guidance data set 109 for the first patient. Such a replacement may be performed whether or not network connections to the patient-affiliated data 105 and/or therapy database 106 were available. In another example, if the first patient is moved to another room of the hospital, it may not be necessary to move the first patient interface device along with the first patient, since a patient interface device in the other room would contain the data necessary to generate a patient-specific guidance data set 109 for the first patient. In another example, the first patient interface device may be moved from patient to patient without the need download new data whenever the patient interface device is moved since the patient interface device may include the data necessary to generate patient-specific guidance data sets 109 for every patient who may receive an infusion. Such advantages may result in fewer total patient interface devices required for a given facility as compared to a facility using patient interface devices that may be dedicated entirely to a single patient during that patient's stay at a facility.

In another example of the operation of the system 100, a physician may order a dose of medication for a patient, and a pharmacy may prepare the dose. When the dosage is prepared, a pharmacist may enter information into a pharmacy database reflecting the preparation of the dose. The patient interface device gateway 104 may receive data from the pharmacy database reflecting the preparation of the dose and the master database 113 may be updated accordingly. Data related to the preparation of the dose may be included in the next journal broadcast of the master database 113 and thereby be communicated to each patient interface device of the plurality of patient interface devices 101 well before the prepared dose has been transported to the patient. Once the dose arrives at the patient, medical personnel may enter patient and dose identification information into a patient interface device and the avatar of the patient interface device may calculate a patient-specific guidance data set 109 for the infusion of the dose into the patient.

In a variation of the present scenario, if between the time the dosage is prepared and the time the patient-specific guidance data set 109 is calculated a change in the patient's condition is detected, the avatar 108 may alter or prevent the dosage from being administered. For example, if renal failure is detected and entered into the facility's records (and subsequently uploaded to the patient interface devices 101) after the dosage has been prepared, but before it has been administered, the avatar 108 may prevent the dosage from being administered. Such prevention may take the form of not performing any infusion of the drug and/or sounding an audible alarm to communicate the danger. This may, for example, be enabled by the logic 115 of the avatar 108 which may not allow the particular medication to be administered where a patient is listed as having renal failure.

In additional examples of the operation of the system 100, the patient interface device 101a may be used to provide continuous administration of a medical fluid. In such a situation, the system 100 may provide several benefits in relation to particular operational scenarios. In a first scenario, during the course of administration of a first unit (e.g., a first IV bag) of medical fluid, the flow rate of the medical fluid may be adjusted from the value prescribed. The patient interface device 101a will record such changes in its memory 119 and communicate such changes to the patient interface device gateway 104. When the first unit is empty, a second unit may be placed in service. In such a situation, the patient interface device 101a may retain knowledge regarding the last used flow rate and begin administering the new unit using that flow rate instead of the prescribed flow rate. Moreover, if for some reason a second patient interface device 101b is used to administer the second unit, it may know the last used flow rate and begin administering the new unit using that flow rate.

In a second scenario, during the course of administration of a first unit of medical fluid under an order for continuous administration of the medical fluid, a physician may order the discontinuance of the administration. Such an order may be entered into the patient interface device 101a or may be entered into the patient-affiliated data 105 and be loaded into the patient interface device 101a database 114 via the patient interface device gateway 104 and master database 113 as described above. However, the pharmacy may have already prepared and sent a second dose to the patient. In such a scenario, the second dose may arrive at the patient, but the patient interface device 101a may prevent it from being administered based on the physician's orders that are reflected in the database 114 of the patient interface device 101a. Moreover, if a second patient interface device 101b is attempted to be used to administer the second unit, the second patient interface device 101b may know the physician's latest orders and also prevent administration of the second dose to the patient.

Since the administration of medical fluids to patients is an event that is communicated back to the master database 113, such information may be available for inventory control purposes. For example, where a dosage of medical fluid was prepared but not administered (as in the examples above), the system 100 may reflect that the dosage was never used and alert the pharmacy that the dosage must be returned to the pharmacy for reuse or destruction. Such a feature may also assist in preventing the theft of dosages where in existing prior art facilities, doses that were prepared but not administered may have been easily stolen since existing systems may not have been able to verify that doses recorded by medical personnel as administered were actually administered. In contrast, the system 100 may only list a dose as being administered if a patient interface device records the actual administration of the dosage. Thus, if no patient interface device reports administration of the dose, the dose may be considered to be not yet administered.

When a patient interface device is first placed into service, it may be provisioned. Provisioning may entail recording the patient interface device's serial number, interconnecting the patient interface device to the network 102, and loading the patient interface device with the avatar 108 and current versions of the database 114 and logic 115.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain known modes of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

What is claimed:

1. A system for use with one or more sources of patient-affiliated data, corresponding with a group of patients who have each been prescribed a medication for infusion pump administration, the system including:

a patient monitor configured to monitor at least one physiological parameter of a select patient from the group of patients;

an infusion pump operable to administer liquid medication to the select patient, wherein the infusion pump includes an input to receive patient identification information and a computer readable memory that stores a database that comprises a plurality of patient records where each patient record of the plurality of patient records corresponds with a different patient of the group of patients and includes at least corresponding patient identification data and patient treatment data comprising prescribed medication data for the corresponding patient, and wherein the computer readable memory of the infusion pump stores logic to utilize a set of rules to:
  select automatically the patient record of the plurality of patient records that is included in the database stored in the computer readable memory of the infusion pump corresponding with patient identification information received at the input of the infusion pump for the select patient;
  create a patient-specific guidance data set for the select patient utilizing the selected patient record of the plurality of patient records corresponding with the select patient, wherein the patient-specific guidance data set is stored in the computer readable memory of the infusion pump and includes infusion parameters related to the prescribed medication data of the selected patient record corresponding with the select patient;
  automatically program the infusion pump to perform administration of medication to the select patient in accordance with the infusion parameters included in the patient-specific guidance data set; and
  update administration of medication to the select patient in response to feedback received from the patient monitor; and
an infusion pump gateway comprising a software program and a server interconnected to the one or more sources of patient-affiliated data and to the infusion pump to:
  update automatically the database stored at the infusion pump utilizing patient-affiliated data corresponding with the group of patients and maintained by the one or more sources of patient-affiliated data.

2. The system of claim 1, wherein the group of patients are patients admitted to a medical care facility.

3. The system of claim 2, wherein the group of patients comprises patients admitted to a particular department of the medical care facility.

4. The system of claim 1, further comprising a pump surveillance database, wherein the infusion pump is adapted to transfer a pump-specific data set to the pump surveillance database, wherein the pump-specific data set includes data related to infusion pump performance.

5. The system of claim 1, wherein the patient-affiliated data comprises at least one database selected from a group consisting of an Electronic Medical Records (EMR) database, a pharmacy database, a hospital medical record database, a medication administration record database, and an admission, discharge and transfer database.

6. The system of claim 1, further comprising:
a therapy database, wherein said server of said infusion pump gateway is interconnected to the therapy database to obtain medication data stored in the therapy database, wherein the computer readable memory of the infusion pump stores said medication data, and wherein said logic of the infusion pump is provided to utilize said medication data in the creation of said patient-specific guidance data set for any given patient of the group of patients.

7. The system of claim 6, wherein the automatic updating of the databases is performed automatically by the infusion pump gateway in response to a change in the patient-affiliated data corresponding with the group of patients, and wherein the logic of the infusion pump is provided to utilize the changed patient-affiliated data in the creation of the patient-specific guidance data set for any given patient of the group of patients.

8. The system of claim 7, wherein the change in the patient-affiliated data originates from the input of the infusion pump.

9. The system of claim 8, wherein the input comprises an input selected from a group consisting of a barcode reader, a card reader, an RFID reader, a keyboard, a touch screen, a data port, and a wireless adapter.

10. The system of claim 7, wherein the change in the patient-affiliated data originates from a source other than the infusion pump.

11. The system of claim 6, wherein the infusion pump is adapted to send data related to performed actions to the one or more sources of patient-affiliated data via the infusion pump gateway.

12. The system of claim 6, wherein the infusion pump gateway comprises:
  a communication link to the one or more sources of patient-affiliated data;
  a communication link to the therapy database;
  a communication link to the infusion pump; and
  a communication link to an external global therapy database.

13. The system of claim 6, wherein the infusion pump gateway comprises a communication link to an external global therapy database.

14. The system of claim 13, wherein the system is adapted to update the therapy database based on changes to the external global therapy database.

15. The system of claim 6, wherein the automatic updating of the databases is performed automatically by the infusion pump gateway in response to a change in the medication data stored in the therapy database, and wherein the logic of the infusion pump is provided to utilize the changed medication data in the creation of the patient-specific guidance data set for any given patient of the group of patients.

16. The system of claim 1, wherein said infusion pump gateway is operative to automatically update said databases on a periodic basis.

17. The system of claim 1, wherein said input of the infusion pump is operable to receive information in the form of a bar code, an RFID tag, a name, a serial number, an identification number, a signal from an embedded identification device, or an identification card.

18. The system of claim 1, wherein the logic of the infusion pump is provided to: create a plurality of patient-specific guidance data sets utilizing said plurality of patient records included in the database stored in the computer readable memory of the infusion pump, wherein the plurality of patient-specific guidance data sets are stored in the computer readable memory of the infusion pump, and wherein each of the plurality of patient-specific guidance data sets corresponds to a different patient of said group of patients.

19. The system of claim 1, wherein the patient monitor is a heart rate monitor.

20. The system of claim 1, wherein updating administration of medication to the select patient in response to feedback received from the patient monitor includes one of reducing an infusion rate and stopping an infusion.

* * * * *